United States Patent [19]

Silverstein et al.

[11] Patent Number: 5,543,294
[45] Date of Patent: Aug. 6, 1996

[54] POLYMERASE CHAIN REACTION/RESTRICTION FRAGMENT LENGTH POLYMORPHISM METHOD FOR THE DETECTION AND TYPING OF MYOBACTERIA

[75] Inventors: Saul J. Silverstein, Irvington; Octavian Lungu, New York; Thomas C. Wright, Jr., Irvington, all of N.Y.

[73] Assignee: The Trustees of Columbia University in the City of New York, New York, N.Y.

[21] Appl. No.: 255,561

[22] Filed: Jun. 8, 1994

Related U.S. Application Data

[63] Continuation of Ser. No. 916,940, Jul. 20, 1992, abandoned, which is a continuation-in-part of Ser. No. 733,109, Jul. 19, 1991, abandoned.
[51] Int. Cl.⁶ ............................. C12Q 1/68; C07H 21/04
[52] U.S. Cl. ............................................. 435/6; 536/24.32
[58] Field of Search ...................... 435/6, 77; 536/24.32

[56] References Cited

PUBLICATIONS

Nagai et al. (1990) Rinsho Byori vol. 38(11): 1247–1253.
Grange (1990) Bull. Int. Union & Tuberclosis & Lung Disease vol. 65 pp. 19–23.
Shinnick (1987) J. Bacteriol. vol. 169(3): pp. 1080–1088.
Mehra et al. (1986) PNAS vol. 83: pp. 7013–7017.
Hance et al. (1989) Mol. Microbiol. vol. 3(7): 843–849.

*Primary Examiner*—George C. Elliott
*Assistant Examiner*—John S. Brusca
*Attorney, Agent, or Firm*—John P. White

[57] ABSTRACT

The subject invention provides a method of diagnosing congenital adrenal hyperplasia in a human subject. The subject invention also provides a method of typing a human papillomavirus in a patient infected by a human papillomavirus. The subject invention further provides a method for detecting Mycobacteria in a clinical sample. Finally, the subject invention provides a method for typing Mycobacteria in a clinical sample containing Mycobacteria.

6 Claims, 10 Drawing Sheets

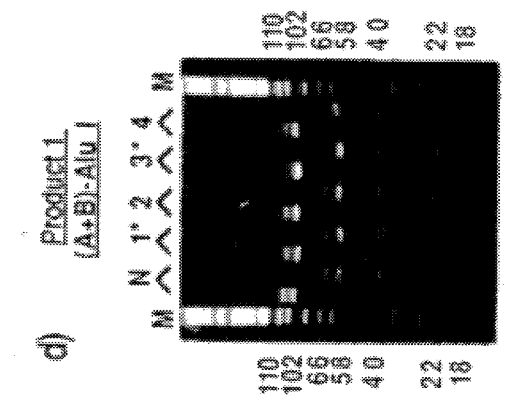
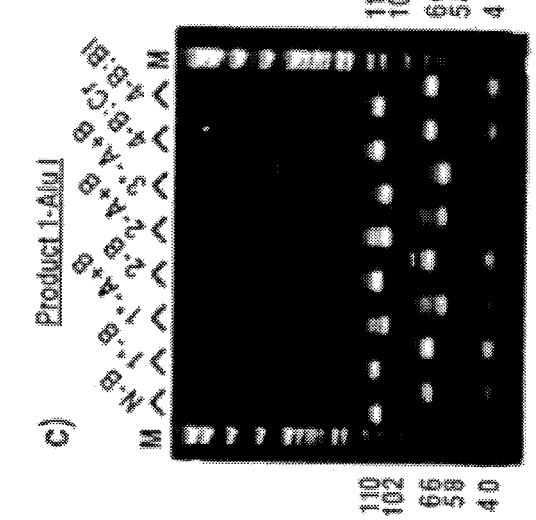
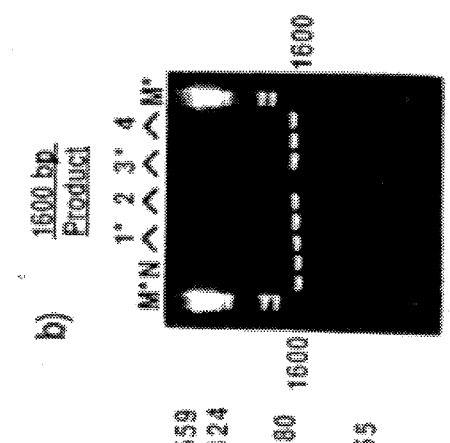
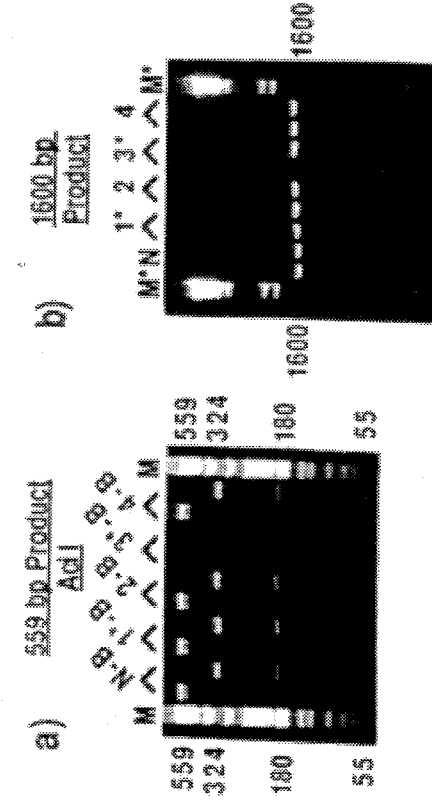

a) 1600 bp B Product b) Product 3-ApaL I c) 1600 bp B Product ApaL I d) Product 4-Bcg I

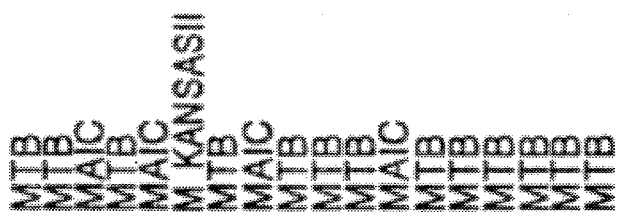
FIGURE 9A
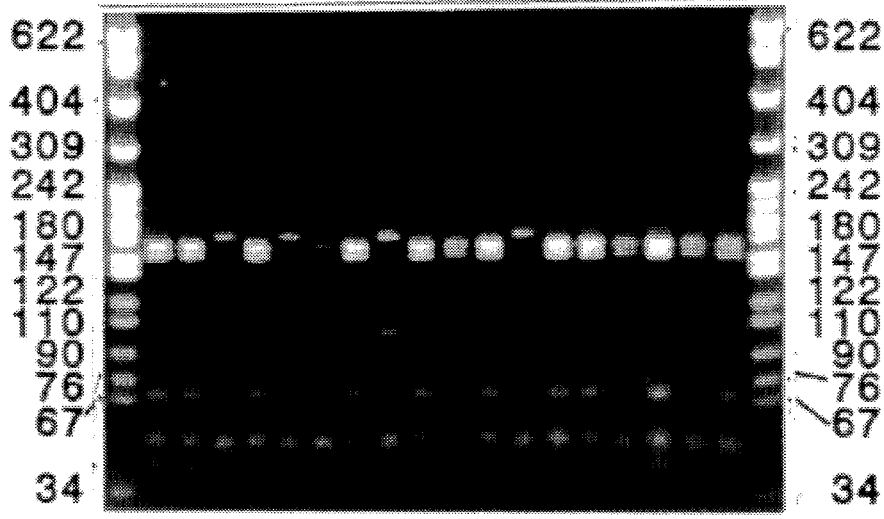
FIGURE 9B
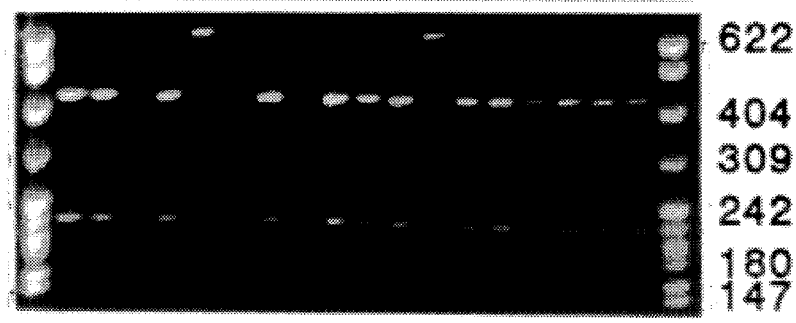

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CTGGCTGGCG CGCGCCTGCT 20

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

ACCCCTGCTT TCTCCCCACC 20

( 2 ) INFORMATION FOR SEQ ID NO:3:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

CATATCTGGT GGGGAGAA 18

( 2 ) INFORMATION FOR SEQ ID NO:4:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

AGTTCCCACC CTCCAGSCCC CA 22

( 2 ) INFORMATION FOR SEQ ID NO:5:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

AGCTTCTTGT GGGCTTTCCA                    20

( 2 ) INFORMATION FOR SEQ ID NO:6:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

TTGAGGAGGA ATTCTCTCTC CTCACCTGGA TCATC    35

( 2 ) INFORMATION FOR SEQ ID NO:7:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

GGCAGGCATG ACGTTGTC                      18

( 2 ) INFORMATION FOR SEQ ID NO:8:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

CCTGGGTTGT AGGGGAGAGG                    20

( 2 ) INFORMATION FOR SEQ ID NO:9:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

CTCTCCTGGG CCGCGATTTT                    20

( 2 ) INFORMATION FOR SEQ ID NO:10:

( i ) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGCCTTTTGC TTGTCCCCAG                  20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CTTCCCAGCA ACCTGGCCAG                  20

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CAATGCCACC ATCGCCGAGG TCCTGC           26

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

ATCCCCAACC CTCGGGAGTC                  20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GAGGAATCAC TTCGCAATGG                  20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i) MOLECULE TYPE: DNA (genomic)

(xi) SEQUENCE DESCRIPTION: SEQ ID NO:15:

ATGTAGCCCT TGTCGAACCG                      20

POLYMERASE CHAIN REACTION/RESTRICTION FRAGMENT LENGTH POLYMORPHISM METHOD FOR THE DETECTION AND TYPING OF MYOBACTERIA

This invention was made with government support under Grant Number CA 23767 (SJS) from the National Institutes of Health. The United States Government has certain rights in this invention.

This application is a continuation of U.S. patent application Ser. No. 07/916,940, filed Jul. 20, 1992, now abandoned, which is a continuation-in-part of U.S. patent application Ser. No. 733,109, filed Jul. 19, 1991, now abandoned.

BACKGROUND OF THE INVENTION

Throughout this application various publications are referenced by Arabic numerals. Full citations for these references may be found at the end of the specification immediately preceding the claims. The disclosure of these publications is hereby incorporated by reference into this application to describe more fully the art to which this invention pertains.

21-Hydroxylase

The adrenal gland and the pituitary gland operate in a feedback loop to produce cortisol. The pituitary gland produces adrenocorticotrophic hormone (ACTH), which stimulates cortisol production by the adrenal gland. Cortisol causes suppression of ACTH production.

In the majority of cases of congenital adrenal hyperplasia, the production of cortisol by the adrenal cortex is impaired because of a defect in, or absence of, the gene for steroid 21-hydroxylase, an enzyme necessary for cortisol synthesis. Because of the failure to produce cortisol, unsuppressed production of ACTH causes the adrenal cortex to make excessive amounts of glucocorticoid related hormones. Some of these hormones act as androgens. As a result, an affected female will have masculinized genitalia at birth. It has been shown that small amounts of glucocorticoids, administered during pregnancy, can suppress fetal adrenal hormone production and prevent these genital abnormalities. In some cases aldosterone production is also impaired. As a result affected individuals develop the most severe form of disease, the salt wasting form of congenital adrenal hyperplasia [1].

The gene encoding 21-hydroxylase is on the short arm of chromosome 6, where a gene (CYP21B), and a pseudogene (CYP21A), alternate with the complement C4 genes [2, 3]. DNA Sequence analysis showed that CYP21B and CYP21A are highly homologous, but several deletions and mutations are present in the pseudogene which render it nonfunctional [4, 5]. Studies using oligonucleotide probes specific for CYP21A and CYP21B, Southern blot/restriction fragment length polymorphism (RFLP), PCR/RFLP or PCR/oligonucleotide probes and sequence analysis of these genes revealed that point mutations, gene deletion, and specific gene to pseudogene conversions are the abnormalities that most often affect the CYP21B alleles in patients with congenital adrenal hyperplasia [6–22].

Most of these methods require the use of molecular hybridization and some are too labor intensive for routine clinical diagnosis or for larer epidemiological studies. We designed and tested, on control human DNA and DNAs prepared from seven patients with congenital adrenal hyperplasia and their family members a method that rapidly and accurately differentiates between the CYP21B and CYP21A genes and conversion events. The method is based on PCR amplification and RFLP analysis of the amplified material; it does not require hybridization analysis, it allows a near perfect discrimination between normal and affected individuals for all of the catalogued abnormalities associated with disease, and it can be easily performed in any laboratory.

Human Papillomavirus

Over the last ten years the association between specific types of human papillomavirus (HPV) and cervical cancers and their precursors has been studied [23–30, 45, 46]. Over 65 different types of HPV have been described and more than 20 of these infect the male and female anogenital tract. Based on their associations with specific types of clinical lesions, the anogenital HPV types have been divided into three classes; low, medium and high oncogenic risk types of viruses [31]. The low oncogenic risk category includes such types as HPVs 6 and 11 which are commonly detected in condylomata acuminata but rarely associated with high-grade cervical intraepithelial neoplasia lesions (CIN) and cancer. The medium oncogenic risk category includes such types as 31, 35 and 45 which are often found in high grade CIN lesions but are only occasionally detected in invasive cancers. Finally, the high oncogenic risk category includes such types as HPVs 16, 18, and 33 which are often found in association with high-grade CIN lesions and cervical cancers.

Despite the potential clinical importance of differentiating between HPV types, current methods for detecting and typing HPV all suffer from serious limitations. Southern blots are considered to be the "gold standard" for HPV testing because of their high sensitivity and capacity to discriminate between the different types of HPV. However, Southern blot hybridization is too labor-intensive for routine clinical testing or for large-scale epidemiological studies. Dot blots are more rapid and easier to perform than Southern blots but are slightly less sensitive and require a large number of different hybridization steps in order to discriminate between individual HPV types. Analysis of the published sequences of human papillomaviruses by Manos and her colleagues [29] revealed a high degree of sequence conservation within the L1 open reading frame (ORF). This homology led to their devising a pair of degenerate "consensus primers" that could be used to amplify virtually any HPV DNA by the polymerase chain method (PCR). PCR with consensus primers allows for rapid detecting of virus sequences in clinical specimens. However, virus typing requires further analysis employing transfer of the reaction products to an immobilized support and multiple rounds of molecular hybridization with "type-specific" probes to discriminate between HPV types. In one recent publication more than 30 type-specific probes were required to discriminate between 17 types of HPV [32].

Detection And Species Identification Of Mycobacteria By PCR-RFLP Analysis

Isolation and identification of mycobacteria species takes several weeks when culturing is required. An alternative method that requires less than 24 hours for identification is enzymatic amplification (PCR) [33] of mycobacterial DNA. However, speciation requires further analysis employing molecular hybridization with "species-specific" probes, analysis that tends to be cumbersome and time consuming. We have devised a rapid and easy method for determining the species of mycobacterium from amplified mycobacterial DNA.

SUMMARY OF THE INVENTION

This invention provides a method of diagnosing congenital adrenal hyperplasia in a human subject which comprises: obtaining a DNA-containing sample from the subject; amplifying seven discrete portions of the subject's 21hydroxylase gene, each such discrete portion containing a sequence that differentiates a wild-type allele from a pseudogene allele; and treating the seven resulting amplified discrete portions of the gene so as to separately determine whether each such portion contains sequence associated with a pseudogene allele, the presence of such a sequence indicating that the subject has congenital adrenal hyperplasia.

This invention also provides a method of typing a human papillomavirus in patient infected by human papillomavirus which comprises obtaining a sample containing DNA from the human papillomavirus to be typed; amplifying the L1 portion of the human papillomavirus DNA; treating the resulting amplified DNA with a plurality of predetermined restriction enzymes so as to produce restriction fragments; and analyzing the fragments so produced so as to type the human papillomavirus.

This invention further provides a method for detecting mycobacteria in a clinical sample, which comprises: a: preparing a sample containing nucleic acid from a clinical sample; b: amplifying the nucleic acid sample using Polymerase Chain Reaction (PCR) with primers selected from known sequences of the groEL gene coding for the 65 kDa antigen of *Mycobacterium tuberculosis* and *Mycobacterium leprae*; c: testing the resulting amplified nucleic acid with a restriction endonuclease to produce restriction fragments; and d: analyzing the nucleic acid fragments so produced using Restriction Fragment Length Polymorphism (RFLP) so as to detect whether the mycobacteria is present.

This invention further provides a method of typing mycobacteria in a clinical sample containing mycobacteria nucleic acid, which comprises: a: preparing a sample containing nucleic acid from a clinical sample containing mycobacteria nucleic acid; b: amplifying the mycobacteria nucleic acid using Polymerase Chain Reaction (PCR) with primers selected from known sequences of the groEL gene coding for the 65 kDa antigen of *Mycobacterium tuberculosis* and *Mycobacterium leprae*; c: testing the resulting amplified mycobacteria nucleic acid with a restriction endonuclease to produce restriction fragments; and d: analyzing the mycobacteria nucleic acid fragments so produced using Restriction Fragment Length Polymorphism (RFLP) so as to determine which type of mycobacteria is present.

Figure 1:
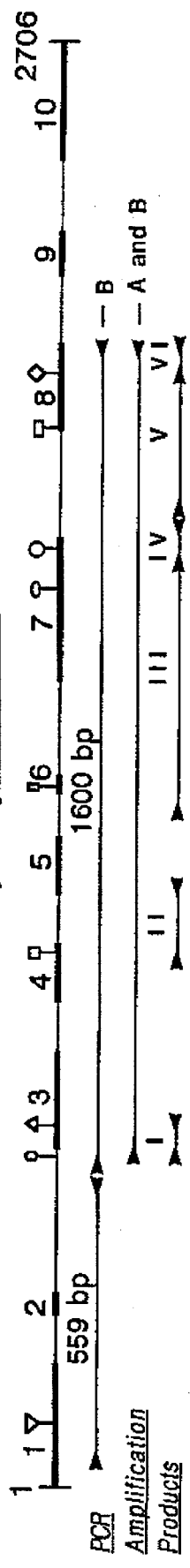
FIG. 1
Figure 1:
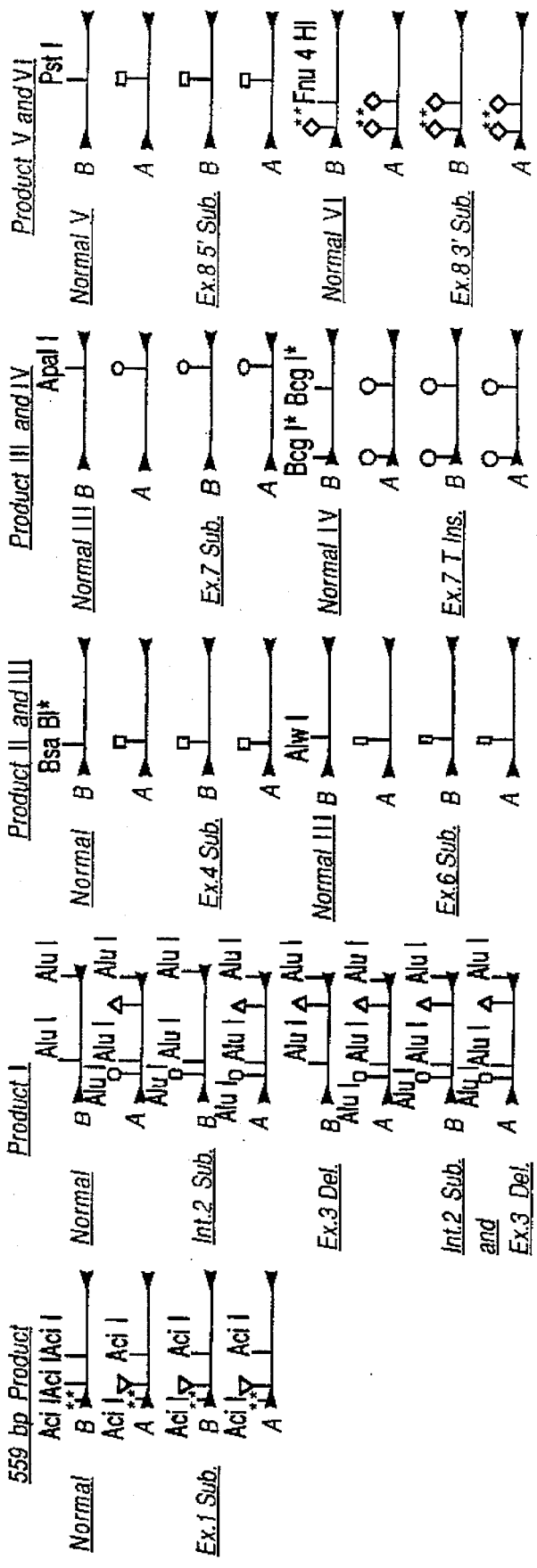

Restriction Endonuclease Cleavage Maps Of The Amplification Targets For The 21-Hydroxylase Genes The published nucleotide sequences of the CYP21A and CYP21B genes were searched for the presence of cleavage sites for restriction endonucleases that distinguish between these genes at specific sites where pseudogene to gene conversions have been identified in patients with congenital adrenal hyperplasia, and for differences that will allow PCR amplification of the gene only, or of both the gene and the pseudogene. Two B—gene specific sets of amplification primers, one A and B—common for gene and pseudogene set of amplification primers and six sets of nested reamplification primers flanking the restriction sites of interest, that are able to amplify DNA from both the 21-hydroxylase gene and its pseudogene, were prepared. The amplification primers and restriction endonucleases are schematically shown in this figure.

FIGS. 2a–2j

Polymerase Chain Reaction (PCR)—Restriction Fragment Length Polymorphism (RFLP) Analysis Of DNA From Normal (N) And A Congenital Adrenal Hyperplasia Family Panel a, 559 bp Product Aci I; Panel b, 1600 bp Product; Panel c, Product 1-Alu I; Panel d, Product 1 (A+B)-Alu I; Panel e, Product 2-Bsa B I; Panel f, Product 3-Alw I; Panel g, Product 3-Apa I; Panel h, Product 4-Bcg I; Panel i, Product 5-Pst I; Panel j, Product 6-Fnu 4 H.

DNA prepared from a chorionic biopsy (Panel 2b and—lane 4 left, Panel 2d—lanes 4 left and right and lanes 4-B:Cr for all the other panels) and from peripheral blood (all other lanes) was analyzed for abnormalities at the 21-hydroxylase locus by PCR-RFLP analysis. The undigested amplification products (left lanes) are presented together with the products of digestion (right lanes) except for Panel 2b where only the undigested products are shown. In Panel 2b the 1600 base pair (bp) CYP21B amplification products (lanes 1, 2 and 3—left and lanes 4—left and right) are presented together with the 1600 bp products resulting from amplification of both the CYP21A and CYP21B genes (1, 2 and 3—right). Lanes designated M contain 4 µg of Msp I digested pBR322 DNA and lanes designated M* contain 1.5 µg of Hind III digested λ DNA. The abnormalities detected are described in the text.

FIG. 3

Polymerase Chain Reaction (PCR)—Restriction Fragment Length Polymorphism (RFLP) Analysis Of DNA From Congenital Adrenal Hyperplasia Patients(2)

DNA prepared from peripheral blood of congenital adrenal hyperplasia patients* or from their family members (lanes designated with numbers) and from a normal individual (lanes N) was analyzed for abnormalities at the 21-hydroxylase locus by PCR-RFLP analysis. In Panels b and d the undigested (left lanes) and digested (right lanes) amplification products are presented together. Only undigested amplification products are shown in Panel a while in Panel c the undigested amplification product is shown only for the normal control (lane N left). In this Figure the 1600 bp products result from CYP21B gene amplification only. As in FIG. 2 lanes designated M contain 4 µg of Msp I digested pBR322 DNA and lanes designated M* contain 1.5 µg of Hind III digested λ DNA. Only informative gels are presented in this figure.

FIG. 4

Restriction Endonuclease Cleavage Maps Of The L1 ORF Target of HPVs

The published nucleotide sequences from amplified region of the L1 ORF of these HPVs were searched for the presence of cleavage sites for the restriction endonucleases Hae III, Pst I and Rsa I and cleavage maps of the putative amplimer were prepared. Where available, plasmids containing clones of the relevant virus genomes were cleaved with these enzymes to verify the location of these sites.

FIG. 5

Restriction Endonuclease Cleavage Patterns Of HPV DNAs

A region of the L1 ORF in plasmid DNAs containing cloned HPV genomes was amplified by PCR using common primers [28]. The amplified DNAs were then incubated for 2 hours in a cocktail of restriction endonucleases containing 10 U each of Hae III, Pst I and Rsa I. After incubation the cleaved DNAs were analyzed by agarose gel electrophoresis as described in Materials and Methods. The lanes identify the virus DNA used in each reaction, the marker lane (M) contains 3.5 μg of MspI digested pBR322 DNA.

FIG. 6

RFLP Analysis Of PCR-Amplified DNAs From Clinical Samples

DNA was isolated from clinical samples and amplified by PCR using consensus primers [28]. Positive samples were typed by incubating the amplified DNAs for 2 hours in a cocktail of restriction endonucleases containing 10 U each of Hae III, Pst I and Rsa I. After incubation, the cleaved DNAs were analyzed by agarose gel electrophoresis as described in Materials and Methods. The lane assignments identify the virus DNA detected in each reaction, the X's denote unknowns and samples with the same X designation contain unknowns with identical cleavage patterns, and the marker lane (M) contains 3.5 μg of MspI-digested pBR322 DNA.

FIG. 7

Restriction Fragment Length Polymorphism (RFLP) Analysis Of DNAs Amplified By Polymerase Chain Reaction (PCR) From Clinical Samples Deoxyribonucleic acid (DNA) was isolated from clinical samples and amplified by polymerase chain reaction using consensus primers [39] previously described [45]. The amplified products were digested with a cocktail of restriction endonucleases and the digestion products were analyzed by electrophoresis in an agarose gel. The lane assignments identify the virus DNA detected in each reaction, the Xs denote unknowns. Samples with the same X designation contain unknowns with identical cleavage patterns. The marker lane (M) contains 3.5 μg of pBR322 DNA digested with MspI.

FIG. 8

Restriction Endonuclease Cleavage Patterns Of Reference Mycobacteria DNAs

A region of the Mycobacterium groEL gene was amplified by PCR using the consensus primers described in the text. The amplified DNAs were then incubated for 2 hours with 20 U of Hae III (Panel A) or Bam HI (Panel B) restriction endonucleases. After incubation the cleaved DNAs were analyzed by gel electrophoresis as described in Materials and Methods. The marker lane contains 4 μg of Msp I digested pBR322 DNA.

FIG. 9

RFLP Analysis Of PCR-Amplified DNAs From Clinical Samples

DNA was prepared from clinical samples and amplified with the consensus primers. The Mycobacteria species were determined by incubating the amplified DNAs for 2 hours with 20 U of Hae III (Panel A) or Bam HI (Panel B) restriction endonucleases and examining the cleaved DNAs by agarose gel electrophoresis. The marker lane contains 4 μg of Msp I digested pBR322 DNA.

DETAILED DESCRIPTION OF THE INVENTION

This invention provides a method of diagnosing congenital adrenal hyperplasia in a human subject which comprises obtaining a DNA-containing sample from the subject; amplifying seven discrete portions of the subject's 21-hydroxylase gene, each such discrete portion containing a sequence that differentiates a wild-type allele from a corresponding pseudogene allele; and treating the seven resulting amplified discrete portions of the gene so as to separately determine whether each such portion contains a sequence associated with the corresponding pseudogene allele, the presence of such a sequence indicating that the subject has congenital adrenal hyperplasia.

For the purposes of this invention, amplification means any method of amplification well known to those of skill in the art. Such methods of amplification include, for example, enzymatic amplification and amplification using conventional cloning techniques well known to those of skill in the art. In one embodiment of the invention, the amplification is effected by enzymatic amplification, e.g., by means of the polymerase chain reaction using seven sets of primers. The method of polymerase chain reaction is well known to those of skill in the art.

In a preferred embodiment of this invention, seven sets of primers are the following:

| Primer | SEQ ID NO | Position |
| --- | --- | --- |
| Ex. 1 - 5' | SEQ ID NO:1 | 34 - 53 |
| IVS 2 B - 3' | SEQ ID NO:2 | 592 - 573 |
| IVS 2 B - 5' | SEQ ID NO:3 | 565 - 582 |
| IVS 2 - 5' | SEQ ID NO:4 | 633 - 654 |
| Ex. 3 - 3' | SEQ ID NO:5 | 742 - 723 |
| Ex. 4 - 5' | SEQ ID NO:6 | 963 - 997 |
| Ex. 5 - 3' | SEQ ID NO:7 | 1139 - 1122 |
| IVS 5 - 5' | SEQ ID NO:8 | 1245 - 1264 |
| Ex. 7 - 5' | SEQ ID NO:9 | 1740 - 1759 |
| IVS 7 - 3' | SEQ ID NO:10 | 1805 - 1786 |
| IVS 7 - 5' | SEQ ID NO:11 | 1807 - 1826 |
| Ex. 8 - 5' | SEQ ID NO:12 | 2077 - 2102 |
| IVS 9 - 3' | SEQ ID NO:13 | 2179 - 2160 |

As used in this invention, a DNA-containing sample is any solution containing human DNA suitable for use in a DNA amplification procedure. The human DNA may be obtained from venous blood, placenta, or any other suitable source.

In a preferred embodiment of this invention, the treating comprises contacting the seven resulting amplified discrete portions of the gene with restriction enzymes so as to produce restriction fragments which permit differentiation of the wild-type allele from a mutated variant. Such means of forming restriction fragments is well known to those of skill in the art [34].

In a preferred embodiment of this invention, the differentiation is effected by means of gel electrophoretic separation of the restriction fragments so produced. Methods of gel electrophoretic separation are well known to those of Skill in the art [34].

In one embodiment of this invention, the human subject is a newborn. In another embodiment of this invention, the human subject is a fetus or an embryo. If the subject is a fetus or embryo, this invention can be used to diagnose the subject as having congenital adrenal hyperplasia while there is still time to either abort or treat the subject. When the subject is a fetus or embryo, a suitable DNA-containing sample may comprise DNA obtained from suitable fetal or embryonic tissue.

This invention provides a method of typing a human papillomavirus in a patient infected by human papillomavirus which comprises obtaining a sample containing DNA from the human papillomavirus to be typed; amplifying the L1 portion of the human papillomavirus DNA; treating the resulting amplified DNA with a plurality of predetermined restriction enzymes so as to produce restriction fragments; and analyzing the fragments so produced so as to type the human papillomavirus. For the purposes of this invention, obtaining human papillomavirus DNA can be done by standard methods well known to those of skill in the art. Analyzing the fragments may be done by methods of size analysis well known to those of skill in the art.

For the purposes of this invention, amplification means any method of amplification well known to those of skill in the art. Such methods of amplification include, for example, enzymatic amplification and amplification using conventional cloning techniques well known to those of skill in the art. In one embodiment of the invention, the amplification is effected by enzymatic amplification, e.g., by means of the polymerase chain reaction. The method of polymerase chain reaction is well known to those of skill in the art.

In one embodiment of this invention, the patient has an a cervical intraepithelial neoplasia. In another embodiment of this invention, the patient has an invasive cervical carcinoma. In another embodiment of this invention, the patient has a benign condylomata.

In one embodiment of this invention, the sample is infected cervical tissue. In another embodiment of this invention, the sample is infected vaginal tissue. In another embodiment of this invention, the sample is infected vulvar tissue. In another embodiment of this invention, the sample is infected anogenital tissue.

In the preferred embodiment of this invention, the amplification is effected by means of the polymerase chain reaction using a plurality of sets of primers. The method of polymerase chain reaction is well known to those of skill in the art.

In the preferred embodiment of this invention, the plurality of predetermined restriction enzymes comprises, for example, Hae III, Pst I and Rsa I. However, any plurality of predetermined restriction enzymes capable of being used to type the human papillomavirus may be used to practice this invention.

In the preferred embodiment of this invention, the fragments are analyzed by means of gel electrophoretic separation of the restriction fragments so produced. Such means are well known to those of skill in the art [34].

This invention also provides a method for detecting mycobacteria in a clinical sample, which comprises:

a: preparing a sample containing nucleic acid from a clinical sample;

b: amplifying the nucleic acid sample using Polymerase Chain Reaction (PCR) with an amplification primer selected from known sequences of the groEL gene coding for the 65 kDa antigen of *Mycobacterium tuberculosis* and *Mycobacterium leprae*;

c: testing the resulting amplified nucleic acid with a restriction endonuclease to produce restriction fragments; and d: analyzing the nucleic acid fragments so produced using Restriction Fragment Length Polymorphism (RFLP) so as to detect whether the mycobacteria is present.

In the method for detecting mycobacteria in a clinical sample, the nucleic acid is selected from the group consisting of DNA and mRNA.

In the method for detecting mycobacteria in a clinical sample, the restriction endonuclease is selected from the group consisting of Hae III and Bam HI.

In the method for detecting mycobacteria in a clinical sample, the clinical sample is a sputum sample.

In the method for detecting mycobacteria in a clinical sample, the amplification primer is selected from the group consisting of

| | |
|---|---|
| SEQ ID NO:14: | 20 |
| GAGGAATCAC TTCGCAATGG | |
| Primer: MB-5' | |
| Position: 236 - 255, and | |
| SEQ ID NO:15: | 20 |
| ATGTAGCCCT TGTCGAACCG | |
| Primer: MB-3' | |
| Position: 844 - 825. | |

This invention also provides a method of typing mycobacteria in a clinical sample containing mycobacteria nucleic acid, which comprises:

a: preparing a sample containing nucleic acid from a clinical sample containing mycobacteria nucleic acid;

b: amplifying the mycobacteria nucleic acid using Polymerase Chain Reaction (PCR) with amplification primer selected from known sequences of the groEL gene coding for the 65 kDa antigen of *Mycobacterium tuberculosis* and *Mycobacterium leprae*;

c: testing the resulting amplified mycobacteria nucleic acid with a restriction endonuclease to produce restriction fragments; and d: analyzing the mycobacteria nucleic acid fragments so produced using Restriction Fragment Length Polymorphism (RFLP) so as to determine which type of mycobacteria is present.

In the method of typing mycobacteria in a clinical sample containing mycobacteria nucleic acid, the nucleic acid is selected from the group consisting of DNA and mRNA.

In the method of typing mycobacteria in a clinical sample containing mycobacteria nucleic acid, the restriction endonuclease is selected from the group consisting of Hae III and Bam HI.

In the method of typing mycobacteria in a clinical sample containing mycobacteria nucleic acid, the clinical sample is a sputum sample.

In the method of typing mycobacteria in a clinical sample containing mycobacteria nucleic acid, the amplification primer is selected from the group consisting of

| | |
|---|---|
| SEQ ID NO:14: | 20 |
| GAGGAATCAC TTCGCAATGG | |
| Primer: MB-5' | |
| Position: 236 - 255, and | |
| SEQ ID NO:15: | 20 |
| ATGTAGCCCT TGTCGAACCG | |
| Primer: MB-3' | |
| Position: 844 - 825. | |

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

EXAMPLE I

21-HYDROXYLASE

Polymerase Chain Reaction (PCR) Amplification

PCR [33] was performed using DNA extracted as previously described [34]. One hundred ng of high molecular weight DNA for the amplification reactions or 1 μl of amplification reaction for the reamplification reactions was added to a 100 µl PCR reaction mixture containing 10 mM Tris HCL (pH 8.3), 50 mM KCl, 1.5 mM MgCl$_2$, 0.01% gelatin, 200 µM of each desoxyribonucleotide triphosphate, 1 µM of each oligonucleotide primer and 2.5 U of Taq DNA Polymerase. One unit of Perfect Match DNA polymerase enhancer (Stratagene, La Jolla, Calif.) was added to the amplification reactions only. All samples were amplified in reactions that contained different sets of the oligonucleotide primers presented in Table 1. Two sets of amplification oligonucleotide primers that will amplify the CYP21B gene only (Ex.1–5'/IVS 2B-3' and IVS 2B-5'/IVS 9-3') or both the CYP21B and the CYP21A genes (IVS 2–5' and IVS 9-3'), and six sets of nested reamplification primers flanking the restriction sites of interest that are able to amplify DNA from both the 21-hydroxylase gene and its pseudogene, were synthesized. The Ex.1–5'/IVS 2B-3' amplification primers and the reamplification primers were chosen so that amplified DNAs from the CYP21B and the CYP21A genes could be easily discriminated when analyzed by RFLP and gel electrophoresis. Each PCR amplification mixture was subjected to 35 cycles of denaturing for 1 minute at 94° C., annealing for 1.5 minutes at 62° C. (amplification reactions) or 50° C. (reamplification reactions), and extension for 1.5 minutes at 72° C. Reactions were initiated by denaturing at 94° C. for 3 minutes and terminated with a final 10 minute elongation step.

Restriction Fragment Length Polymorphism (RFLP) Analysis Of PCR Products

A 20 µl aliquot was removed from each PCR reaction and after the addition of 2.5 µl of the recommended 10 X digestion buffer the amplified or reamplified DNAs were digested for 2 hours with 10 U of restriction endonucleases (NE Bio Labs, Beverly, Mass.). The sites for the enzymes used to digest each PCR product are schematically shown in FIG. 1. The undigested (15 µl of the remaining amplification/reamplification reactions) and digested (entire digestion reaction) DNAs were then analyzed by electrophoresis at 100 V in a 1% (1600 bp product) or 3.5% (all other PCR products), 4/1 Nu Sieve/Sea Plaque GTG agarose gel, containing 0.2 µg/ml of ethidium bromide and prepared in Tris Borate (89 mM Boric Acid and 1 mM Na$_2$EDTA).

Results And Discussion

Design Of Oligonucleotide Primers And Selection Of Restriction Endonucleases

To ascertain the feasibility of using PCR amplification coupled with RFLP analysis for the identification of mutations at the 21-hydroxylase locus that result in congenital adrenal hyperplasia we first examined the published DNA sequences of the 21-hydroxylase gene and it pseudogene [4, 5] for restriction endonuclease cleavage sites and for differences that will allow PCR amplification of the CYP21B only or of both the CYP21B and the CYP21A genes. Restriction endonuclease cleavage maps for CYP21B and CYP21A were then prepared and aligned for comparison. Endonucleases that differentiate the functional gene from the pseudogene were identified for six of the nine catalogued mutations. Where discriminating restriction endonucleases sites were absent, in two of the nine catalogued mutations, differentiating sites were created by the modification of the 3' end of the reamplification primers [35, 36]. The nucleotide sequence and location of the oligonucleotide primers are presented in Table 1 while the PCR amplification products and the restriction endonucleases sites are schematically shown in FIG. 1.

A 559 bp and a 1600 bp fragment of the CYP21B gene only were amplified. This approach will detect homozygous deletion of the entire gene and is necessary for the subsequent detection of heterozygous mutations by RFLP analysis. In a parallel reaction 1600 bp fragments from both the gene and its pseudogene are amplified to be certain that the DNA can be amplified.

The C-T mutation in the first exon causing nonclassic steroid 21-hydroxylase deficiency [6] is detected with the Ex.1–5'/IVS 2B-3' set of primers. These primers amplify a 559 bp fragment of the CYP21B gene only. Digestion of this product with Aci I results in three fragments of 324, 180 and 55 bp. A C-T conversion event in exon 1 of the CYP21B gene will delete one of the Aci I cleavage sites, thus, Aci I digestion of the 559 bp product amplified from a converted CYP21B gene will result in only two fragments of 324 and 235 bp. Table 2A and Table 2B present the Aci I digestion pattern in normal and in heterozygous or homozygous CYP21B exon 1 conversions.

The first set of reamplification nested primers (IVS 2–5'/Ex.3—3') detects an A/C-G transversion in the second intron that leads to aberrant splicing of pre mRNA [19], and an 8 bp deletion in exon 3 which results in a frame shift [4, 5]. When amplified CYP21B and CYP21A DNA from a normal individual is reamplified with this set of primers, four fragments, two of 110 bp and two of 102 bp in size are produced. The 110 bp fragments result from amplification of the CYP21B alleles and the 102 bp products are derived from the CYP21A alleles. The size difference results from an 8 bp deletion in exon 3 of the pseudogenes. Therefore, if the CYP21B genes have been homozygously converted in this exon reamplification of this region they will yield four 102 bp products. An heterozygous deletion can accurately be detected only if the products of the CYP21B genes are used for reamplification. In this case two fragments, one of 110 bp (normal allele) and the other of 102 bp (converted allele) are produced. The CYP21A genes contain an Alu I site in intron 2 as a result of the transversion. CYP21B alleles converted in this region will contain an additional Alu I site within IVS 2, thus, Alu I digestion of product 1 DNA can detect such a transversion. The Alu I digestion pattern of CYP21B genes and of CYP21B and CYP21A genes in normal and in homozygous or heterozygous intron 2 transversions is presented in Table 2A and Table 2B.

No restriction site is introduced or deleted by the T-A transversion in exon 4 of the CYP21A genes that substitutes an Asn for an Ile in the putative amino acid sequence at position 172 [4, 5]. Therefore, an artificial cleavage site for the Bsa BI restriction endonuclease in the CYP21B genes only was created by substituting a C for a G and a G for a T at the 3' end of the sense reamplification primer of set two. Reamplification of both gene and pseudogene amplified DNAs with set two nested primers (Ex.4–5'/Ex.5-3') produces a fragment of 176 bp. The two products of the CYP21B gene are digested with Bsa BI into four fragments; two of 144 bp and two of 32 bp. Resistance to cleavage with this restriction endonuclease indicates the presence of the T-A transversion found in the CYP21A alleles. It can be detected by the size of the cleaved amplification products as shown in Table 2A and Table 2B.

The third set of nested primers (IVS 5—5'/IVS 7-3') amplify a 560 bp fragment from exons 6 and 7 in each gene. The resulting amplification products can be differentiated by cleavage with various restriction endonucleases. For example, Alw I and Apal I digest the products of the CYP21B genes only. These endonucleases distinguish between the gene and its pseudogene for a cluster of mutations in exon 6 (Alw I) [4, 5] and a point mutation at bp 1683 in exon 7 (Apal I) [17]. The Alw I and Apal I digestion products of these genes are shown in Table 2A and Table 2B for normal and for individuals with homozygous or heterozygous mutations in this region.

The gene to pseudogene conversion that occurs in exon 7, where a single T insertion is present in the pseudogene at position 1716 [4, 5], can be detected with the fourth set of nested primers (Ex.7-5'/IVS 7-3') as previously described [36]. The 3' end of the 5' reamplification primer was modified to create a cleavage site for the Bcg I restriction endonuclease in the CYP21B genes only. As a result of this insertion the fragments reamplified from the CYP21B alleles and from the CYP21A alleles differ by one bp; 66 for CYP21B and 67 CYP21A. Because only the 66 bp fragment is cleaved with Bcg I, this restriction endonuclease can differentiate between a normal allele and one with a T insertion in the CYP21B genes at this location (Table 2A and Table 2B).

The fifth set of nested primers (IVS 7-5'/IVS 9-3') was designed to detect a C-T transition at position 1995 of the pseudogene in the eighth exon [4, 5, 20]. The Pst I restriction endonuclease cleaves the two 372 bp products generated by PCR amplification of the CYP21B genes in half, resulting in four 186 bp fragments. The transition, in CYP21A destroys the Pst I recognition site. Therefore, a conversion event in this region of CYP21B results in amplification products that cannot be digested with Pst I (Table 2A and Table 2B).

Fnu 4HI and the sixth set of nested primers (Ex.8-5'/IVS 9-3') are used to differentiate between CYP21B and CYP21A for a C-T transition mutation in exon 8 at position 2108 of the CYP21A. Only the 103 bp reamplification products of CYP21B are cleaved with Fnu 4HI, while the reamplification products of CYP21A are not. Thus, gene conversions across this region of CYP21B can be differentiated from a wild type allele by digestion of amplified CYP21B sequences with Fnu 4HI. The Fnu 4HI digestion pattern of the six products is presented in Table 2A and Table 2B.

Analysis Of Clinical Specimens

DNAs extracted from a normal individual and from several patients with congenital adrenal hyperplasia and some of their family members were examined for abnormalities at the 21-hydroxylase locus by PCR amplification and RFLP analysis of the amplified material.

FIG. 2 presents analysis of a family where the mother (lanes 1) is affected with the late onset form of disease and a child (lanes 3) is affected with the salt wasting form of congenital adrenal hyperplasia. The father (lanes 2), and a second child (lanes 4) whose 21-hydroxylase genes were analyzed in both DNA extracted from a chorionic biopsy and from peripheral blood lymphocytes (as described in the figure legend) are phenotypically normal.

DNA prepared from a normal control and from the family described above was first amplified with the CYP21B gene specific primers, and with the CYP21A and CYP21B common amplification primers. The DNA prepared from the patient with the salt wasting form of disease could not be amplified with the CYP21B specific primers (FIG. 2a—lanes 3 left and FIG. 2b—lane 3 left). This result coupled with the demonstration that a 1600 bp product was amplified from the same DNA with the gene—pseudogene common primers (FIG. 2b—lane 3 right) indicates that both copies of CYP21B are deleted or converted to CYP21A in this patient's DNA.

The 559 bp product RFLP presented in FIG. 2a shows that the mother, the father and the unaffected child have at least one normal allele of the CYP21B gene in this region. Their RFLP patterns were identical with those of DNA from a normal individual for this product.

The patterns generated by reamplification of the 1600 bp products with the first set of nested primers are shown in FIG. 2c, and FIG. 2d represents the patterns obtained using the first set of nested primers to amplify genomic DNA prepared from this family. RFLP analysis indicates that the first child has both the substitution in IVS 2 and the 8 bp deletion in exon 3, in all of his CYP21 genes, as deduced from the absence of the 110, 66, and 40 bp fragments in this analysis (FIG. 2c and FIG. 2d—lanes 3). Judging from the difference in intensity of the fragments generated by gene and pseudogene amplification and Alu I digestion [110 and 66 bp (CYP21B) versus 102 and 58 bp (CYP21A)], it appears that the 21-hydroxylase genes of the mother (lanes 1), the father (lanes 2), and the phenotypically normal child (lanes 4) contain sequences derived from both the CYP21A and CYP21B genes in this region (FIG. 2c—lanes 1 and 3, and FIG. 2d—lanes 1, 2 and 4). The 22 and 18 bp fragments are not shown in FIG. 2c.

Figure 2G:
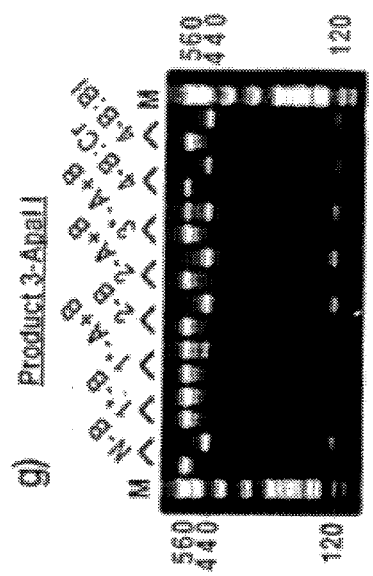
Figure 2J:
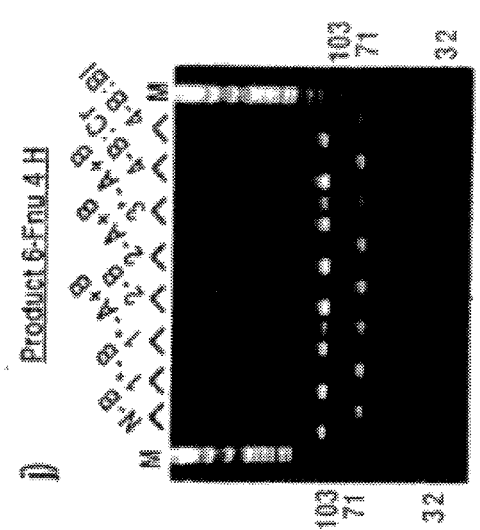
Figure 2F:
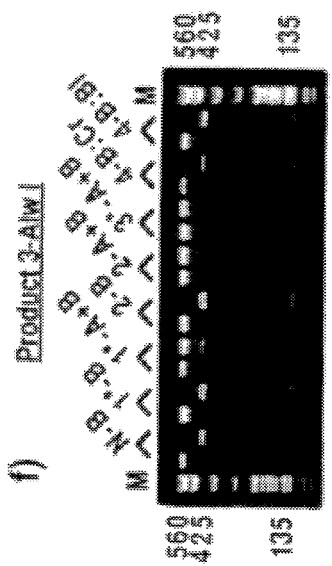
Figure 2I:
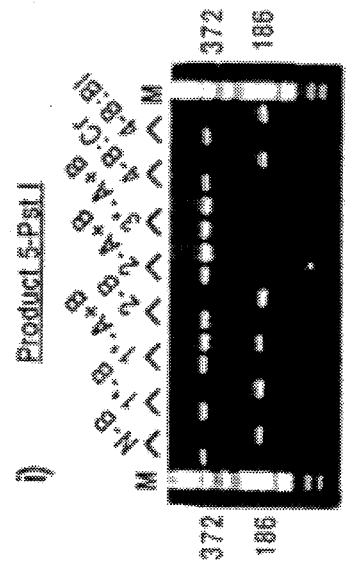
Figure 2E:
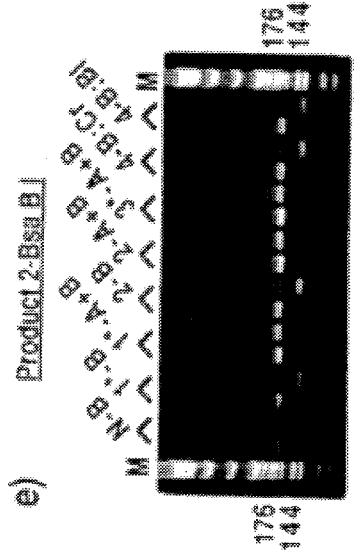
Figure 2H:
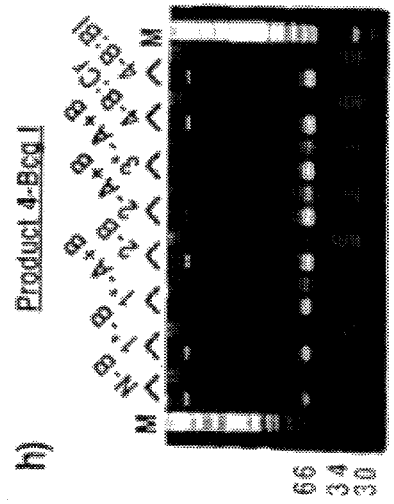

Product 2-Bsa BI analysis of DNA from members of this family shows the absence of the 144 bp fragment in the amplification product of DNA from the salt wasting child (FIG. 2e—lane 3 right). Thus, this individual is homozygous for the exon 4 mutation. The mother, father and the second child contain at least one copy of this region of the CYP21B gene because digestion of their reamplified CYP21B DNA results in the appearance of a 144 bp fragment that is diagnostic of the wild type sequence (FIG. 2e—lanes 1B, 2B and 4Bs right). Interestingly, and seemingly in contrast to these findings, when both the CYP21A and the CYP21B genes are reamplified and analyzed for this mutation, it appears that the mother and father are homozygous for this mutation as deduced by the absence of the 144 bp fragment in FIG. 2e—lanes 1 and 2 A+B right. This aberration is explained by preferential reamplification of the CYP21A genes with this set of nested primers. The 32 bp digestion product is not shown for this product.

Analysis for the substitution in exon 6 is presented in FIG. 2f. The presence of the 425 bp fragment in the digestion products from each member of this family reveals that one of the CYP21B alleles is preserved in this region in the DNA of all members of this family. Therefore, at least one copy of the affected childs' CYP21A gene contains CYP21B sequences. The 425 bp fragment is faint in this sample (FIG. 2f—lane 3 right), suggesting heterozygosity for B sequences in this region. The 135 bp fragments are difficult to detect in FIG. 2f—lanes 2(A+B) and 3(A+B) right.

Further analysis of this family indicates that the CYP21B sequences(s) of the mother has lost the Apal I site in exon 7 as both the 440 and the 120 bp fragments are absent when CYP21B reamplified DNA is digested with Apal I (FIG. 2g—lane 1 B right). However, at least one of her CYP21A alleles has sequences from the CYP21B gene, because both the 440 and 120 bp fragments are present when the CYP21A and CYP21B reamplification products are digested with Apal I (FIG. 2g—lane 1 A+B right). These results suggest that a reciprocal exchange event occurred in this region; one or more of the CYP21A genes has acquired CYP21B sequences. Only CYP21B sequences are present in this region of the fathers DNA because the 560 bp fragment is absent after digestion of DNA reamplified from both CYP21A and CYP21B genes (FIG. 2g—lane 2 A+B right). Therefore, in the father all CYP21A sequences are converted to CYP21B. Both children have at least one copy of normal CYP21B DNA in this region.

All family members contain a Bcg I site in the product IV reamplification of either the CYP21B allele (FIG. 2h—lanes 1, 2, and 4B) or in the CYP21A alleles of the salt-wasting child (FIG. 2h, lanes 3 A+B) because the 34 and 30 bp fragments are present in all digested reamplification products.

Similarly, a Pst I site is present in the product V reamplification of each member of this family as demonstrated by the presence of a 186 bp fragment in all digested products in Panel i of FIG. 2.

The 71 and 32 bp fragments identified in all Fnud 4H digested reamplification products (FIG. 2j) indicate that CYP21B sequences are present in this region of amplified DNA in each member of this family. Both of the fathers' CYP21A genes are converted to CYP21B sequences at the site of the 3' mutation in exon 8 because the 103 bp fragment that is indicative of CYP21A sequences is absent from reamplification products of both the CYP21A and CYP21B genes (FIG. 2j, lane 2 (A+B).

Analysis of another family, where one member has the nonclassical form of congenital adrenal hyperplasia (FIG. 3—lanes 2), his unaffected mother (FIG. 3—lanes 1) and two sisters (FIG. 3—lanes 3 and 4) are shown together with the analysis of three patients with the salt wasting form of congenital adrenal hyperplasia; two siblings (FIG. 3—lanes 5 and 6) and an unrelated patient (FIG. 3—lanes 7).

For diagnosis it is only necessary to amplify the CYP21B allele. The CYP21B specific amplification primers were able to amplify the 559 bp product (data not shown) and the 1600 bp product (FIG. 3a) from DNA extracted from all the individuals studied, therefore only analysis of the CYP21B genes are presented. None of the described abnormalities at the CYP21B gene locus were detected in the DNA from the patient with the nonclassical form of congenital adrenal hyperplasia patient or in the DNA prepared from his family members, or in the DNA prepared from another patient with the nonclassical form of disease whose DNA was examined separately (data not shown). Their RFLP patterns were identical with those of DNA from a normal individual for all PCR reamplification products.

Figure 3A:
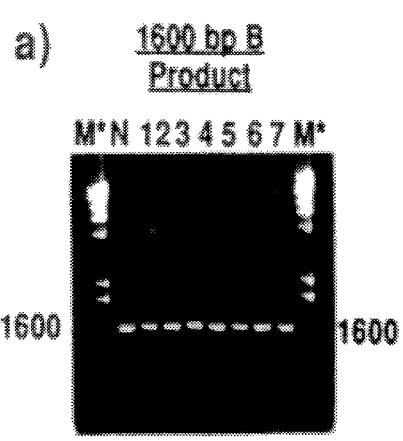
Figure 3B:
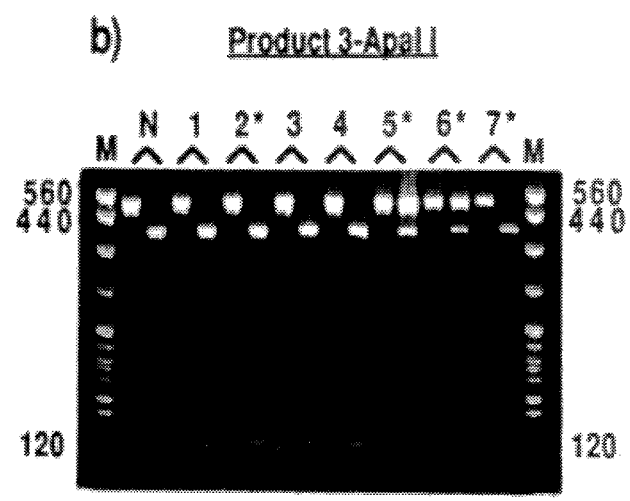
Figure 3C:
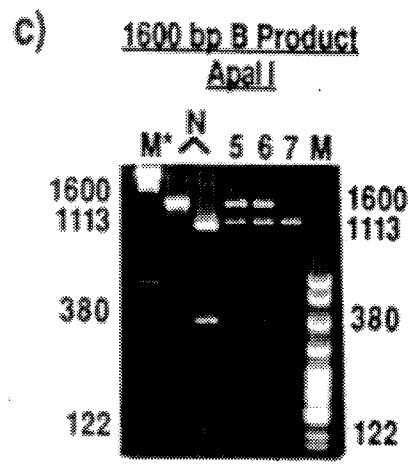

One of the CYP21B alleles in the siblings with salt wasting syndrome has CYP21A sequences in exon 7 at the Apal I site. This conclusion was reached because RFLP products diagnostic of both CYP21A (560 bp fragment) and CYP21B (440 and 120 bp fragments) were detected in the products of reamplification using the third set of nested reamplification primers (FIG. 3b—lanes 5 and 6 right). These data were confirmed when fragments diagnostic of both CYP21A [1493 (comigrating with the 1600 bp fragment) and 122 bp fragments] and CYP21B [113, 380 and 122 bp fragments] RFLPs were detected when the 1600 bp B-specific amplification products of these patients were digested with Apal I (FIG. 3c—lanes 5 and 6). The CYP21B gene RFLP patterns of normal and patient 7 DNA are also presented (FIG. 3c—lanes N and 7).

Figure 3D:
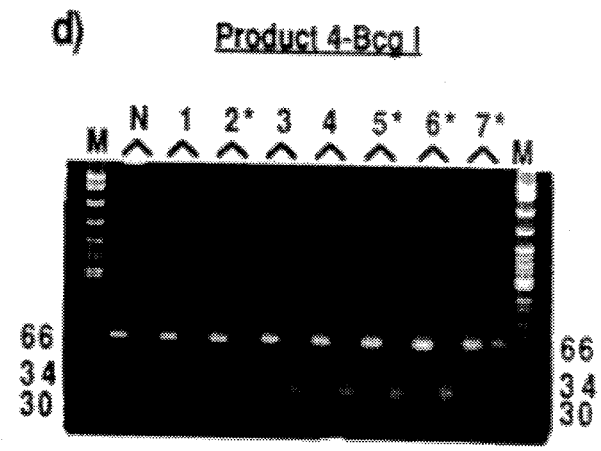

Another salt wasting patient that we studied has the T insertion in exon 7 in one of his CYP21B genes and as a result the CYP21A specific 67 bp fragment is detected in the Bcg I digestion pattern of amplified DNA (FIG. 3d—lane 7 right). The presence of the 34 and 30 bp fragments (CYP21B RFLP) indicates that his other 21-hydroxylase B gene is normal in this region. The 2 bp fragments of Bcg I digestion (FIG. 3d) cannot be detected in this analysis.

In summary, PCR-RFLP analysis of DNA from the first family (FIG. 2) demonstrated that the 21-hydroxylase genes of the affected child are homozygous for both the substitution in intron 2 and the 8 bp deletion in exon 3. Analysis of this family also identified the molecular defect present in the mothers' DNA, who has non-classical disease and carries the HLA14,DR1 haplotype. All of her CYP21B genes have the point mutation in exon 7, a mutation associated with HLA14,DR1 haplotype and the nonclassical form of congenital adrenal hyperplasia (16). Analysis of DNA prepared from the chorionic biopsy and from peripheral blood lymphocytes of the other sibling showed identical RFLP patterns for all PCR products, and as predicted by the chorionic biopsy DNA analysis, this child is not affected by congenital adrenal hyperplasia. This indicates that he inherited a normal CYP21B gene from his father who has one normal CYP21B allele.

The phenotypic expression of congenital adrenal hyperplasia requires homozygous mutations in both alleles of the 21-hydroxylase B gene. Therefore, the heterozygous abnormalities that we identified in the salt wasting patients examined in FIG. 3 do not explain their disease. Since the method utilized in this study detects all of the described mutations at this locus the "unaffected" CYP21B allele of these patients must contain unique undescribed mutations. Furthermore, the mutation in exon 7, detected in the DNA prepared from the salt-wasting siblings (FIG. 3b and FIG. 3c, lanes 5 and 6) is associated with the late onset form of disease [16]. If this mutation is also associated with the salt-wasting syndrome, or if both of these patients CYP21B alleles contain other mutations, can only be confirmed by sequence analysis of their genes.

In conclusion, we were able to identify defects at the 21-hydroxylase gene locus in one of three patients with the nonclassical form and in all salt wasting congenital adrenal hyperplasia patients that we studied. Surprisingly, and contrary to the findings of another larger study that identified the homozygous described mutations in 80 to 90% of congenital adrenal hyperplasia patients, we were able to demonstrate homozygosity in only two of seven patients studied. Since we analyzed only a limited number of patients, this discrepancy may result from the selected population of patients that we studied. However, it is probable that uncatalogued mutations are present in a larger percentage of congenital adrenal hyperplasia patients than described. The method that we used to detect mutations at this locus, is not based on hybridization analysis and therefore is not influenced by stringency conditions. The use of RFLP analysis is superior for detection of heterozygosity in these genes. Larger epidemiological studies using this method of detection are necessary to determine the extent of homo versus heterozygosity at these alleles, and further DNA sequence analysis will be required to determine if there are other, as yet unidentified, mutations that contribute to the congenital adrenal hyperplasia phenotype.

TABLE 1

| | Oligonucleotide Primers For Amplification | |
| --- | --- | --- |
| Primer | SEQ ID NO and Sequence | Position |
| Ex. 1 - 5' | SEQ ID NO:1<br>CTGGCTGGCG CG*CGCCTGCT | 34 - 53 |
| IVS 2 B - 3' | SEQ ID NO:2<br>ACCCCTGCTT TCTCCCCACC | 592 - 573 |
| IVS 2 B - 5' | SEQ ID NO:3<br>CATATCTGGT GGGGAGAA | 565 - 582 |
| IVS 2 - 5' | SEQ ID NO:4<br>AGTTCCCACC CTCCAG(G/C)CCC CA | 633 - 654 |
| Ex. 3 - 3' | SEQ ID NO:5<br>AGCTTCTTGT GGGCTTTCCA | 742 - 723 |

TABLE 1-continued

Oligonucleotide Primers For Amplification

| Primer | SEQ ID NO and Sequence | Position |
|---|---|---|
| Ex. 4 - 5' | SEQ ID NO:6<br>TTGAGGAGGA ATTCTCTCTC<br>CTCACCTGG*A T*CATC | 963 - 997 |
| Ex. 5 - 3' | SEQ ID NO:7<br>GGCAGGCATG* AC*GTTGTC | 1139 - 1122 |
| IVS 5 - 5' | SEQ ID NO:8<br>CCTGGGTTGT AGGGGAGAGG | 1245 - 1264 |
| Ex. 7 - 5' | SEQ ID NO:9<br>CTCTCCTGGG CCGC*GA*TTTT | 1740 - 1759 |
| IVS 7 - 3' | SEQ ID NO:10<br>AGCCTTTTGC TTGTCCCCAG | 1805 - 1786 |
| IVS 7 - 5' | SEQ ID NO:11<br>CTTCCCAGCA ACCTGGCCAG | 1807 - 1826 |
| Ex. 8 - 5' | SEQ ID NO:12<br>CAATGCCACC ATCGCCGAGG<br>TC**CTGC | 2077 - 2102 |
| IVS 9 - 3' | SEQ ID NO:13<br>ATCCCCAACC CTCGGGAGTC | 2179 - 2160 |

In Table 1, the sequences and positions were determined using the data from Higashi, Y., Yoshioka, H., Yamana, M., Gotoh, O., and Fujii-Kurijama, Y., Complete nucleotide sequence of two steroid 21-hydroxylase genes tandemely arranged in human chromosome 6: a pseudogene and a genuine gene, *Proceedings of the National Academy of Science, USA,* 1986; vol. 83, pages 2841–2845, (Reference 4).

In Table 1, the B primers are complementary to the active 21-OH B gene DNA only.

In Table 1, the 5' primers are sense while 3' primers are antisense.

In Table 1, * denotes a nucleotide substitution that creates a restriction endonuclease site, while In Table 1, ** denotes a base substitution that removes a restriction endonuclease site.

TABLE 2A

Fragment Size Of The Undigested (UD) And Digested (D) PCR Amplification Products In Normal And Homozygous Mutations

| | | A + B | B |
|---|---|---|---|
| Normal 559 - | UD | 4x559 | 2x559 |
| Aci I | D | 4x324,2x235,<br>2x180,2x55 | 2x324,2x180,<br>2x55 |
| Ex. 1 Sub. - | UD | 4x559 | 2x559 |
| Aci I | D | 4x324,4x235 | 2x324,2x235 |
| Normal I - | UD | 2x110,2x102 | 2x110 |
| Alu I | D | 2x66,2x58,2x40,<br>2x22,2x18,4x4 | 2x66,2x40,2x4 |
| Int.2 Sub. - | UD | 2x110,2x102 | 2x110 |
| Alu I | D | 2x66,2x58,4x22,<br>4x18,4x4 | 2x66,2x22,2x18,<br>2x4 |
| Ex.3 Del. - | UD | 4x102 | 2x102 |
| Alu I | D | 4x58,2x40,2x22,<br>2x18,4x4 | 2x58,2x40,2x4 |
| Int.2 Sub + | UD | 4x102 | 2x102 |
| Ex.Del. - | D | 4x58,4x22,4x18, | 2x58,2x22,2x18, |
| AluI | | 4x4 | 2x4 |
| Normal II - | UD | 4x176 | 2x176 |
| Bsa BI | D | 2x176,2x144,<br>2x32 | 2x144,2x32 |
| Ex.4 Sub. - | UD | 4x176 | 2x176 |
| Bsa BI | D | 4x176 | 2x176 |
| Normal III - | UD | 4x560 | 2x560 |
| Alw I | D | 2x560,2x425,<br>2x135 | 2x425,2x135 |

TABLE 2A-continued

Fragment Size Of The Undigested (UD) And Digested (D) PCR Amplification Products In Normal And Homozygous Mutations

| | | A + B | B |
|---|---|---|---|
| Ex. 6 Sub. - | UD | 4x560 | 2x560 |
| Alw I | D | 4x560 | 2x560 |
| Normal III - | UD | 4x560 | 2x560 |
| Apal I | D | 2x560,2x440,<br>2x120 | 2x440,2x120 |
| Ex. 7 Sub. - | UD | 4x560 | 2x560 |
| Apal I | D | 4x560 | 2x560 |
| Normal IV - | UD | 2x67,2x66 | 2x66 |
| Bcg I | D | 2x67,2x34,2x30,<br>2x2 | 2x34,2x30,2x2 |
| Ex. 7 T Ins. - | UD | 4x67 | 2x67 |
| Bcg I | D | 4x67 | 2x67 |
| Normal V - | UD | 4x372 | 2x372 |
| Pst I | D | 2x372,4x186 | 4x186 |
| Ex. 8 5' Sub. - | UD | 4x372 | 2x372 |
| Pst I | D | 4x372 | 2x372 |
| Normal VI - | UD | 4x103 | 2x103 |
| Fnu4HI | D | 2x103,2x71,2x32 | 2x71,2x32 |
| Ex. 8 3' Sub. - | UD | 4x103 | 2x103 |
| Fnu4HI | D | 4x103 | 2x103 |

In Table 2A, A denotes 21-OH pseudogene, while B denotes 21-OH gene.

TABLE 2B

Fragment Size Of The Undigested (UD) And Digested (D) PCR Amplification Products In Normal And Heterozygous Mutations

| | | A + B | B |
|---|---|---|---|
| Normal 559 - | UD | 4x559 | 2x559 |
| Aci I | D | 4x324,2x235,<br>2x180,2x55 | 2x324,2x180,2x5 |
| Ex. 1 Sub. - | UD | 4x559 | 2x559 |
| Aci I | D | 4x324,3x235,180,<br>55 | 2x324,235,180,<br>55 |
| Normal I - | UD | 2x110,2x102 | 2x110 |
| Alu I | D | 2x66,2x58,2x40,<br>2x22,2x18,4x4 | 2x66,2x40,2x4 |
| Int.2 Sub. - | UD | 2x110,2x102 | 2x110 |
| Alu I | D | 2x66,2x58,40,<br>3x22,3x18,4x4 | 2x66,40,22,18,<br>2x4 |
| Ex.3 Del. - | UD | 110,3x102 | 110,102 |
| Alu I | D | 66,3x58,2x40,<br>2x22,2x18,4x4 | 66,58,2x40,2x4 |
| Int.2 Sub + | UD | 110,3x102 | 110,102 |
| Ex. Del. - | D | 66,3x58,40,<br>3x22,3x18,4x4 | 66,58,2x22,<br>2x18,2x4 |
| AluI | | | |
| Normal II - | UD | 4x176 | 2x176 |
| Bsa BI | D | 4x176,2x144,<br>2x32 | 2x144,2x32 |
| Ex.4 Sub. - | UD | 4x176 | 2x176 |
| Bsa BI | D | 3x176,144,32 | 176,44,32 |
| Normal III - | UD | 4x560 | 2x560 |
| Alw I | D | 2x560,2x425,<br>2x135 | 2x425,2x135 |
| Ex. 6 Sub. - | UD | 4x560 | 2x560 |
| Alw I | D | 560,425,135 | 560,425,135 |
| Normal III - | UD | 4x560 | 2x560 |
| Apal I | D | 2x560,2x440,<br>2x120 | 2x440,2x120 |
| Ex. 7 Sub. - | UD | 4x560 | 2x560 |
| Apal I | D | 560,440,120 | 560,440,120 |
| Normal IV - | UD | 2x67,2x66 | 2x66 |
| Bcg I | D | 2x67,2x34,<br>2x30,2x2 | 2x34,2x30,2x2 |
| Ex. 7 T Ins. - | UD | 3x67,66 | 67,66 |
| Bcg I | D | 3x67,34,30,2 | 67,34,30,2 |
| Normal V - | UD | 4x372 | 2x372 |
| Pst I | D | 2x372,4x186 | 4x186 |

TABLE 2B-continued

Fragment Size Of The Undigested (UD) And Digested (D)
PCR Amplification Products
In Normal And Heterozygous Mutations

|  |  | A + B | B |
|---|---|---|---|
| Ex. 8 5' Sub. | UD | 4x372 | 2x372 |
| Pst I | D | 3x372,2x186 | 372,2x186 |
| Normal VI - | UD | 4x103 | 2x103 |
| Fnu4HI | D | 2x103,2x71,2x32 | 2x71,2x32 |
| Ex. 8 3' Sub. - | UD | 4x103 | 2x103 |
| Fnu4HI | D | 3x103,71,32 | 103,71,32 |

In table 2B, A denotes 21-OH pseudogene, while B denotes 21-OH gene.

EXAMPLE II

HUMAN PAPILLOMAVIRUS

Reference:

Example II, Human Papillomavirus, is described in Reference 45: Lungu, O., Wright, Jr., T. C., and Silverstein, S., Typing Of Human Papillomaviruses By Polymerase Chain Reaction Amplification With L1 Consensus Primers And RFLP Analysis, *Molecular And Cellular Probes*, 1992, vol. 6, pages 145–152.

Methods

Specimens

DNA samples from three different sources were used. One source was from cervico-vaginal lavages of patients attending a colposcopy clinic. Cells from the lavages were pelleted and the DNA extracted as described below. Another source was frozen unfixed tissue biopsies from patients with either vulvar lesions clinically considered to be condyloma or from laryngeal condylomas. The final source of DNA was from formalin-fixed, paraffin-embedded biopsies of anogenital lesions histologically diagnosed as being HPV-related. The majority of these biopsies were obtained during a colposcopic work-up of an abnormal Pap smear (females) or by peniscopy during the examination of the partners of patients with cervical intraepithelial neoplasia (males). All paraffin-embedded biopsy materials were placed in 10% buffered formalin within 5 minutes of sampling and fixed for 5–17 hours.

Southern Blots Of HPV

DNA from frozen, unfixed biopsies was extracted according to standard methods [37] and HPV DNA was analyzed by Southern blots as previously described [38]. In brief, 5 to 15 μg of total cellular DNA was digested with Pst I overnight, electrophoresed on a 1% agarose gel, transferred to a nylon membrane and baked at 80° C. for 2 hours. The filter was then hybridized using a probe mixture containing equimolar amounts of 32P-labelled HPV 16, 18, and 35 DNAs, each at a specific activity of at least $1\times10^8$ dpm/μg. Filters were washed at low stringency (Tm-40° C.) and exposed to X-ray film. HPV type was determined on the basis of the mobility of the digested fragments.

DNA Extraction And Polymerase Chain Reaction Amplification

PCR was performed using either purified DNA or extracts from paraffin-embedded tissues and the consensus sequence HPV primers of Manos et al. [29]. For paraffin-embedded biopsies, three 10 micron sections were taken from the paraffin block, placed in a microfuge tube and 150 μl of digestion buffer (50 mM Tris pH 8.5, 1 mM EDTA, 0.5% Tween 20) containing 200 μg/ml Proteinase K was added. Sections were then incubated for 2 hours at 65° C. As soon as the samples are heated to 65° C. the paraffin melts and separates from the aqueous phase. At the end of the digestion, the samples were centrifuged for five minutes in a microfuge at full speed. This process pellets the undigested tissue and completely separates the aqueous phase containing the DNA from the paraffin phase. The aqueous phase was removed and stored at −20° C.

In the initial studies using hybridization to detect PCR products, PCR reaction mixtures were prepared according to the protocol of Ting and Manos [39]. 10 μl of sample were added to a 100 μl reaction mixture containing 50 mM KCl, 4 mM $MgCl_2$ 10 mM Tris pH 8.5, 200 μM dNTPs, 500 ng of each PCR primer, and 2.5 U of Taq DNA polymerase (Perkin-Elmer Cetus). In subsequent reactions and when PCR products were analyzed by RFLP, 1.5 mM $MgCl_2$ was used. All samples were tested initially using control Ki-ras specific primers. These primers yield a 157 base pair product [40]. Only samples which yielded a PCR product after amplification with the Ki-ras primers were analyzed for HPV DNA using PCR.

The PCR mixture was overlaid with paraffin oil and subjected to 35 cycles of amplification using either an automated thermocycler (Perkin-Elmer Cetus Corp) or manually through water baths. Each cycle consisted of a heating step at 92° C. for 1 minute (DNA denaturation), followed by an incubation at 52° C. for 1.5 minutes (primer annealing) and subsequent incubation at 72° C. (chain elongation) for 1.5 minutes.

To type the PCR products using hybridization, 10 μl of the amplification products were electrophoresed on agarose gels and transferred to nylon membranes. DNA was detected by hybridization using "consensus" or "type-specific" oligonucleotide probes labeled with $^{32}P$ using $\gamma$-$^{32}$P-ATP and polynucleotide kinase. Hybridization conditions for these probes were as described in Ting and Manos [39].

Restriction Fragment Length Polymorphism (RFLP) Analysis Of PCR Products

To determine if HPV DNA was present, one tenth of the amplification reaction was then analyzed by electrophoresis at 100 V in a 3.5%, 3/1 Nu Sieve/Sea Plaque GTG agarose gel, containing 0.5 μg/ml of ethidium bromide, prepared in Tris-Borate (89 mM Tris, 89 mM Boric Acid and 1 mM $Na_2EDTA$). To type the product by RFLP analysis, DNA from each HPV-positive sample, as determined by gel UV visualization, was precipitated with ethanol, washed with 70% ethanol, lyophilized and resuspended in 18 μl of 1 X restriction enzyme digestion buffer containing 10 mM Tris-HCL (pH 7.9), 10 mM $MgCl_2$, 50 mM NaCl and 1 mM DTT. Two μl of a cocktail containing 10 U each of Hae III, Pst I and Rsa I restriction endonucleases (NE Bio Labs, Beverly, Mass.) were then added and the mixture was incubated at 37° C. overnight. The entire restriction endonuclease reaction was then analyzed by gel electrophoresis as described above.

Results And Discussion

Selection Of Restriction Endonucleases

Figure 4:
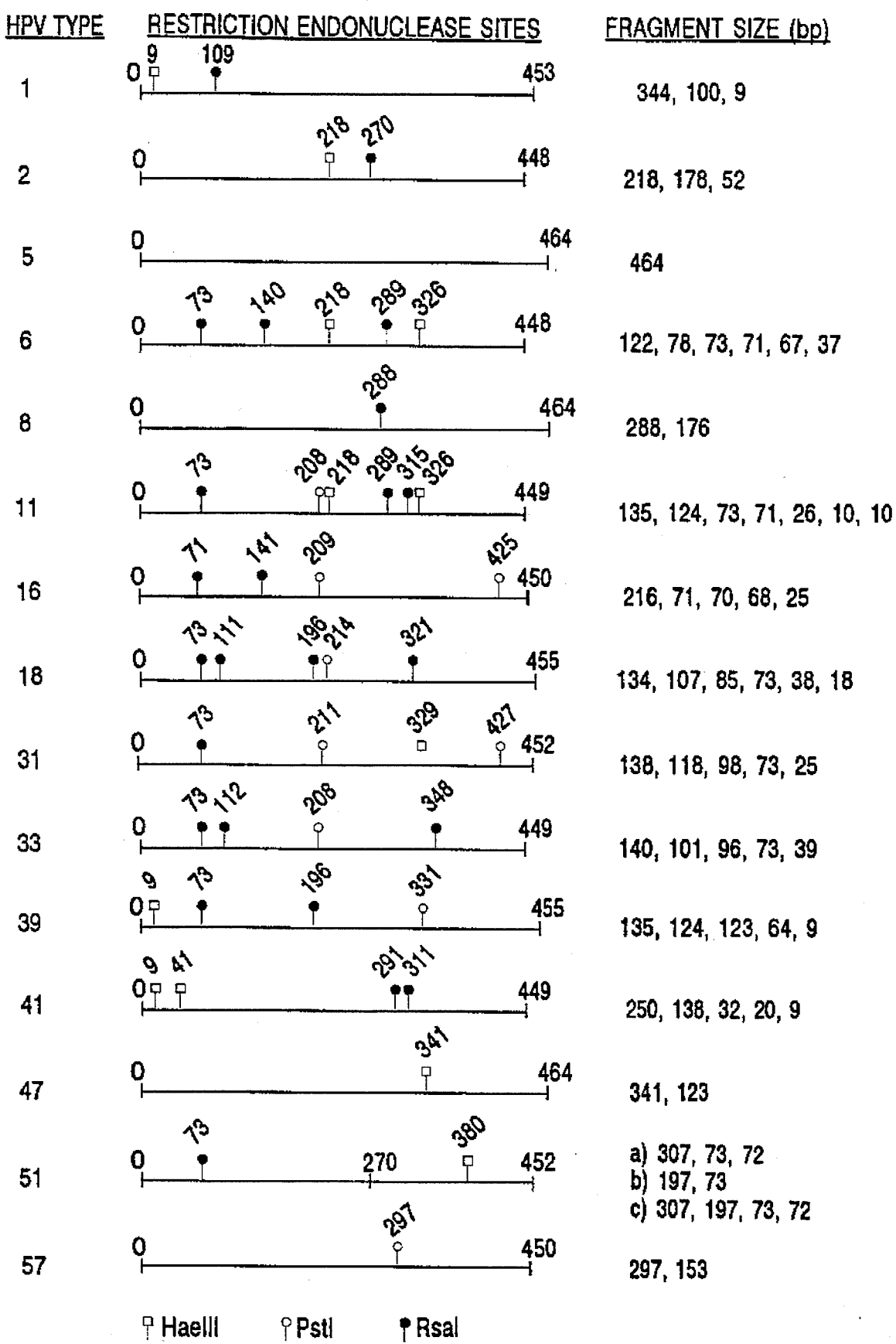
Figure 5:
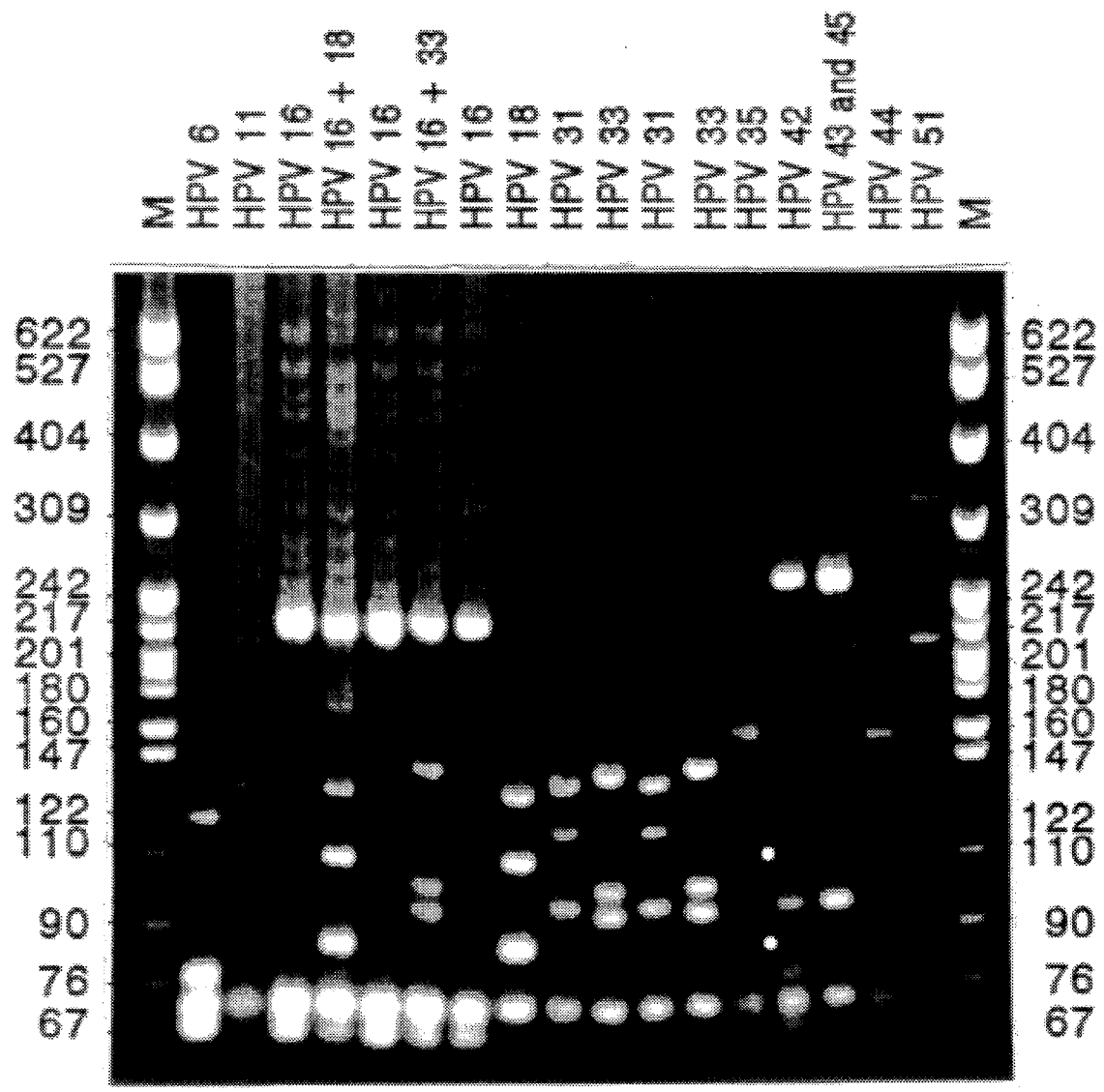

Ting et al. [39] suggest that HPV amplimers of the L1 region could be typed on the basis of their restriction endonuclease digestion patterns. To ascertain the feasibility of this typing approach, we first examined the published DNA sequences of various virus isolates for the presence of restriction endonuclease cleavage sites within the region of L1 that is amplified by PCR using the primers described by Manos et al [29]. Restriction endonuclease cleavage maps for each genome were prepared and aligned for comparison. Where a particular sequence was not available, plasmids containing the cloned genome were amplified and the restriction endonuclease digestion pattern was empirically determined. Computer simulations and restriction endonuclease cleavage analyses of plasmid DNAs suggested that use of Hae III, Pst I and Rsa I restriction endonucleases, in combination, could differentiate between almost all sequenced HPV types and the majority of other types of HPV that were examined in this study (FIGS. 4 and 5). The exceptions were HPVs 43 and 45 which displayed identical cleavage patterns in this analysis (FIG. 5).

Amplification of HPV 51 DNA generated two products; one of 452 bp which was similar in size to what is amplified in other HPVs, and another of 272 bp which results from mispriming of the MY09 primer within L1. We have previously determined the basis for mispriming and demonstrated that it is a function of the annealing temperature [41]. In our analyses, this was the only DNA which consistently generated multiple products after PCR amplification. A consequence of the generation of multiple PCR products is the appearance of more than the predicted number of fragments in the RFLP analysis. Thus, RFLP analysis of HPV 51 amplimers might yield 2, 3, or 4 fragments depending on whether, one or another or both amplification products are made (FIGS. 4 and 5). In all instances examined, the RFLP pattern was consistent with the computer analysis or the experimentally-derived cleavage pattern (FIG. 5).

The digestion conditions were designed to provide 80–100% activity for each enzyme in the cocktail and, when used in mock-typing experiments, showed very few partial products. However, in some cases partial digestion products were unavoidable. In these instances it is important to be able to differentiate between partial digestion products and multiple amplimers arising from either mispriming, as with HPV 51, or the presence of DNA from more than one virus type in the sample. Therefore, in these instances it is important to: i) know the digestion pattern of the various HPV types; ii) sum the molecular weights of the products; and iii) carefully study the gel for submolar fragments to differentiate among these possibilities. For example, in FIG. 5 (HPV 35 lane, white dots) two fragments were generated as a result of partial digestion, whereas in the lanes marked HPV 16+18, and 16+33 there are multiple fragments which result from cleavage of both amplimers. In other experiments, digestion of the HPV 35 amplimer yielded the correct digestion pattern for this DNA which consists of only the two higher molecular weight and the 73 bp fragments. To help identify fragments generated by partial digestion, we included an amplified control DNA that should be cleaved by all enzymes used in the typing.

Although the intensity of any ethidium bromide-stained band should be proportional to the molecular weight of the cleavage product, we have noted that, on occasion, some of the fragments in the photographic reproduction are faint when examined. They are visible when the UV-illuminated gel is examined directly. However, photographic reproduction is not always faithful. This is especially important when the typing results are not interpreted by the same individual who performed the typing and visualized the gel. An example is shown in FIG. 5 (lane HPV 44); here, two fragments of 160 and 73 bp are readily seen while a third fragment of 120 bp, which is generated after cleavage of the HPV 44 amplimer and which was visible after staining by UV illumination, was not detectable in the photograph of the gel shown in FIG. 5. Therefore, for accurate documentation of faint bands, it is important that an overexposed photograph of each typing gel is provided. Finally, we note that there is 100% concordance between the restriction nuclease digestion patterns predicted by computer mapping of sequenced HPVs and experimental RFLP analysis of DNAs amplified from plasmids containing cloned virus genomes.

Typing Of Clinical Specimens

DNA extracted from 98 clinical samples was examined for the presence of HPV sequences and these samples were typed by the PCR-RFLP method to determine the feasibility of this approach. The DNAs in these samples were previously examined for HPV DNA and had been typed by PCR amplification and blot hybridization analysis of the products, or by Southern blot analysis of DNA. The samples were analyzed for the presence of HPV DNA by PCR amplification of the L1 region and were typed by RFLP analysis of the PCR product as described in Methods.

Figure 6:
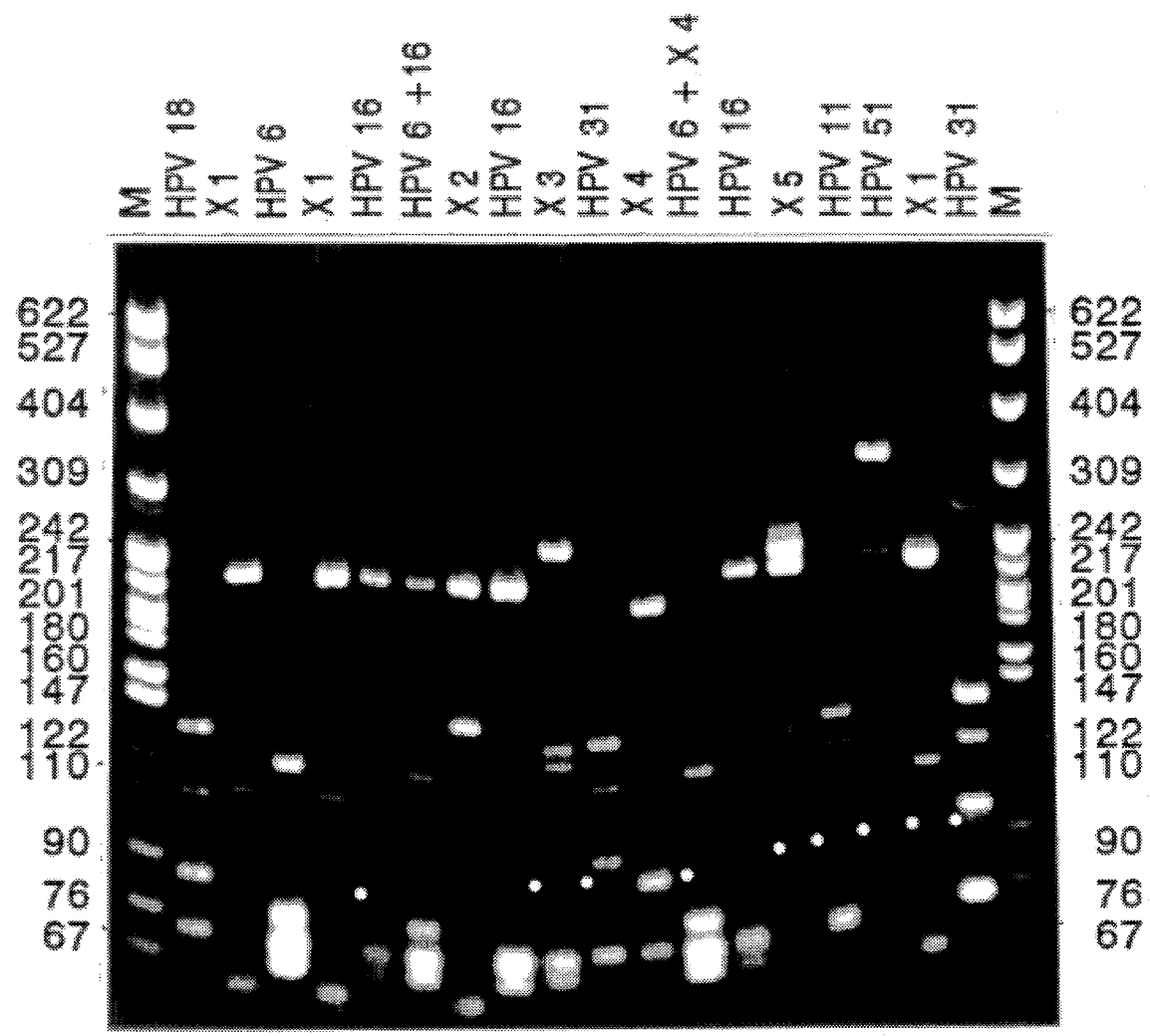

RFLP analysis of 18 specimens is shown in FIG. 6. This analysis reveals both the exquisite sensitivity of the method and some of the potential pitfalls. For example, in two instances, we noted the presence of multiple virus types in the specimen. In one instance the sample contained HPVs 6 and 16, and this was also observed in the Southern Analysis of tissue DNA. However, in another instance we noted that DNA from both HPV 6 and another novel strain were amplified. The novel strain was not detected by Southern analysis. In other instances, RFLP analysis has clarified the origin of weakly hybridizing bands on Southern blots by demonstrating that they arose from the presence of DNA from novel HPVs in the sample.

A potential problem that sometimes interferes with RFLP typing of clinical specimens is non-specific amplification. The fragments that are flanked by white dots in FIG. 6 result from non-specific amplification. They are present and migrate to the same position in gels containing the undigested amplimer (data not shown). When multiple HPV types are present in a specimen, there is potential for preferential PCR amplification of only one of the types. This could result in misdiagnosis and failure to report the presence of a second type when multiple types are present. This is less of a problem with Southern blots where detection is theoretically proportional to the absolute amount of each type present in the specimen, providing that enough probes are available for the identification of multiple types. Another potential pitfall is the presence of point mutations in the original specimen or those which arise during amplification. These could result in either gain or loss of a restriction endonuclease site and the attendant problems in typing. While there are other potential pitfalls, such as mistyping and failure to amplify, we have not found these to occur frequently. Moreover, in our hands this technique is more sensitive and significantly easier to perform than either Southern blot analysis of total DNA extracted from clinical samples, or hybridization analysis of amplified DNA with type-specific probes. Our results with these 98 samples are summarized in Table 2.

TABLE 2

Correlation Between PCR-RFLP Analysis And Other Typing Techniques

| PCR/RFLP | Southern Blot | | PCR/Hybridization | |
|---|---|---|---|---|
| | + | − | + | − |
| + | 37 | 1 | 39 | 0 |
| − | 3 | 10 | 0 | 0 |
| ? | 4 | 0 | 4 | 0 |

In Table 2, Concordant Samples: +/+ indicates that the samples were shown to contain HPV DNA in each instance, and where there were multiple HPV types, at least one common type was detected by each method of analysis; –/– indicates the sample did not contain HPV DNA by either method of analysis.

In Table 2, Discordant Samples: –/+ indicates that HPV DNA was not detected in the sample by PCR/RFLP analysis but that HPV DNA was detected and could be typed by the other method of analysis; ? indicates that interpretation of the PCR/RFLP product was not possible.

Briefly the data can be summarized as follows; there was an 86% agreement between the PCR/RFLP assay and Southern blot hybridization. In four instances where the results were discordant, it was because; the amplified DNA could not be digested (1 case), or there was insufficient sample for further analysis (1 case), or the two techniques identified different HPV types in the sample (2 cases). For the four other samples that were at variance, one was Southern blot hybridization-negative and the other three were Southern blot hybridization-positive and not amplifiable by PCR. The concordance between PCR/Hybridization and PCR/RFLP was 91%. Two of the differences were in typing the amplimers. In the other two cases, blot hybridization using probes for HPVs 6, 11, 16, 18 and 33 failed to detect a known HPV type in the amplimers, whereas RFLP detected HPV 16 in the sample.

In summary, PCR/RFLP analysis of DNA from clinical samples offers a rapid and sensitive test for the identification and typing of HPV DNA. The technique is limited, in terms of typing, by the polymorphisms found in the highly conserved region within the L1ORF of HPVs.

Conclusion

Human Papillomaviruses (HPV) cause benign and malignant lesions of the epithelial and mucosal surfaces. Certain virus types are associated with invasive cervical carcinomas [23–25], while others are associated with benign condylomata [26–28]. We have developed a rapid method for determining HPV type that is based on restriction fragment length polymorphism (RFLP) analysis within the L1 region of HPVs that is amplified by PCR using the consensus primers described by Manos et al. [29]. Analysis of the products generated by PCR amplification of plasmids containing cloned HPV genomes and of 88 clinical specimens, known to contain HPV viral DNA by previous hybridization analysis, revealed that this method is useful for typing HPV sequences amplified from a variety of sources including cervical lavages, fresh tissue, and paraffin-embedded formalin-fixed biopsy material. The method can differentiate between most known types of HPV and discriminate between infections with single, multiple or novel HPV types. A high correlation (86%) was obtained when this method was compared with PCR amplification and Southern Blot hybridization analysis of PCR product or South Blot hybridization analysis of total genomic DNA. Differences in typing occurred mostly for specimens that contained multiple or new, unknown HPV types. However, RFLP typing easily identified repeated patterns for new HPV types that were not detected by the other methods. In summary, PCR-RFLP typing is a sensitive and specific method of rapidly identifying and characterizing HPV DNA in clinical specimens from a variety of sources.

EXAMPLE III

RELATIONSHIP OF HUMAN PAPILLOMAVIRUS TYPE TO GRADE OF CERVICAL INTRAEPITHELIAL NEOPLASIA

Reference:

Example III, Relationship Of Human Papillomavirus Type To Grade Of Cervical Intraepithelial Neoplasia, is described in Reference 46: Lungu, O., Sun, X. W., Felix, J., Rechart, R. M., Silverstein, S., Wright, Jr., T. C., Relationship Of Human Papillomavirus Type To Grade Of Cervical Intraepithelial Neoplasia, *Journal of the American Medical Association*, 1992; vol. 267, pages 2493–2496.

Over the last decade an enormous amount of evidence has accumulated implicating human papillomavirus (HPV) in the pathogenesis of cervical cancer and its precursors [30, 47]. Despite the incontrovertible associations between HPV and the development of cervical disease, the clinical applicability of this relationship has yet to be defined. The failure to incorporate these molecular advances into clinical practice has been due to many factors including the relative insensitivity of the commercially available HPV detection tests and the paucity of large-scale clinical studies demonstrating the clinical relevance of HPV typing. Another confounding factor has been the large number of HPV types that have been isolated from anogenital lesions.

In the mid 1980's, when fewer types of HPV had been described, it was frequently suggested that specific associations between particular types of HPV and specific histopathological types of lesions existed [48, 25]. Human papillomavirus types 6 and 11 were considered to be "low oncogenic risk" viruses since they were frequently detected in exophytic, benign condylomas but very rarely detected in cervical intraepithelial neoplasia (CIN) 3 and invasive cancers. In contrast, types 16 and 18 were considered to be "high oncogenic risk" viruses since they were often detected in CIN 2, CIN 3, and invasive cancers, but only rarely in CIN 1 and condylomata. This line of thinking led to the proposition that screening women for "high-risk" HPV types would identify those women at increased risk for developing cervical cancer [31, 49]. However, as more than 60 types of HPV came to be identified, and as it became recognized that a significant number of healthy women with normal Papanicolaou smears harbored high-risk HPV types, the hypothesis that there are specific associations between certain types of HPV and specific lesions was considered to be overly simplistic and the entire concept of HPV DNA testing as a clinical practice began to be questioned [50, 51]. The loss of interest in HPV DNA typing as a clinical test occurred despite the fact that relatively few studies had been published analyzing the types of HPV associated with a large number of CINs of different grades, and despite the fact that many of the studies that had been published used methods, such as in situ hybridization, that are relatively imprecise for typing HPV.

To clarify the associations between specific types of HPV and specific grades of CIN better, we have used a new, highly accurate method for typing HPV to analyze 276 histologically well-characterized, HPV DNA-positive cases of CIN [45]. The method used to discriminate between different HPV types is based on restriction fragment length polymorphism (RFLP) analysis of amplimers produced during polymerase chain reaction (PCR) amplification of the conserved L1 region of HPV using consensus primers [39]. This method allows discrimination between most known types of HPV and can be applied to a variety of specimens, including paraffin-embedded material. The results obtained using this method are simpler to interpret than those obtained using either Southern blot or in situ hybridization. With this method, little heterogeneity of HPV types was detected in CIN 2 and CIN 3, but a high degree of heterogeneity was detected in CIN 1.

Materials And Methods

The DNA from cervicovaginal saline lavages, cervical swabs, and frozen, unfixed or formalin-fixed, paraffin-embedded biopsy tissue obtained during a colposcopic workup of patients with abnormal Papanicolaou smears was extracted according to standard methods [45, 39], and the HPV DNA was analyzed as previously described [45]. In brief, DNA was amplified with the L1 consensus primers of Manos [39] and the amplification product was digested with a combination of Hae III, Pst I, and Rsa I restriction endonucleases. The digestion reaction was then analyzed by electrophoresis in a 3.5% GTG agarose gel (FMC Bioproducts, Rockland, Me.), and the HPV type was determined according to the RFLP pattern as visualized after ethidium bromide staining using ultraviolet light. Only samples that gave a strong enough signal to be detected clearly on ethidium bromide-stained gels after digestion with restriction enzymes were analyzed for HPV type. Only 16% of the samples in which HPV was detected lacked a strong enough signal to type. Fifteen of the samples with sufficient signal to be analyzed were frozen tissues from loop electrosurgical excisional biopsies; 231 were formalin-fixed, paraffin-embedded cervical biopsies obtained with a punch biopsy forceps; eight were cervical swabs; and 22 were purified DNAs isolated form cervicovaginal lavages.

All cervical biopsy specimens were reviewed and graded by a single pathologist who was blinded as to HPV status. Standard histopathologic criteria were used to assign a grade to the lesion [52]. This study was approved by the Institutional Review Board of the College of Physicians and Surgeons of Columbia University.

Results

The HPV types detected in the 276 cases of HPV DNA-positive CIN are summarized in Table 3. The CIN 1 lesions were very heterogeneous with regard to associated HPV types. Nineteen percent of lesions classified as CIN 1 contained HPV types that could not be classified by PCR-RFLP analysis. These unclassified HPV types include eight different "novel" types that were detected in multiple cases, but which do not correspond to any of the types that we can identify, including types 1, 2, 3, 6, 8, 10a, 11, 12, 14, 15, 16, 17, 18, 19, 20, 21, 22, 24a, 31, 33, 34, 35, 39, 41, 42, 43, 44, 45, 47, 51, 55a, and 57 [45]. As previously reported by other investigators [53–55], we found that only a small percentage (19%) of lesions classified as CIN 1 are associated with HPV 6 or 11 either alone or in combination with other HPV types; HPV types 16, 18, or 33 were detected in 29% of the lesions classified as CIN 1. In 19% of the cases these HPVs were detected as individual types and in 10% they were detected in combination with other types.

In contrast, lesions classified as CIN 2 or 3 were much more restricted with regard to HPV types (Table 3). In most cases (88%), HPV types 16, 18, or 33 were detected either alone or in combination with other types. Novel HPV types were detected in only 4% of CIN 2 and 3 lesions compared with 19% of CIN 1 lesions. In a comparison of HPV types in CIN 2 or CIN 3 lesions, there were no differences in distribution of HPV types (Table 3). Eighty-five percent of CIN 2 lesions contained HPV 16, 18, or 33, whereas 89% of CIN 3 lesions contained these HPV types. A single case of CIN 2 contained HPV types 6 or 11 alone.

Figure 7:
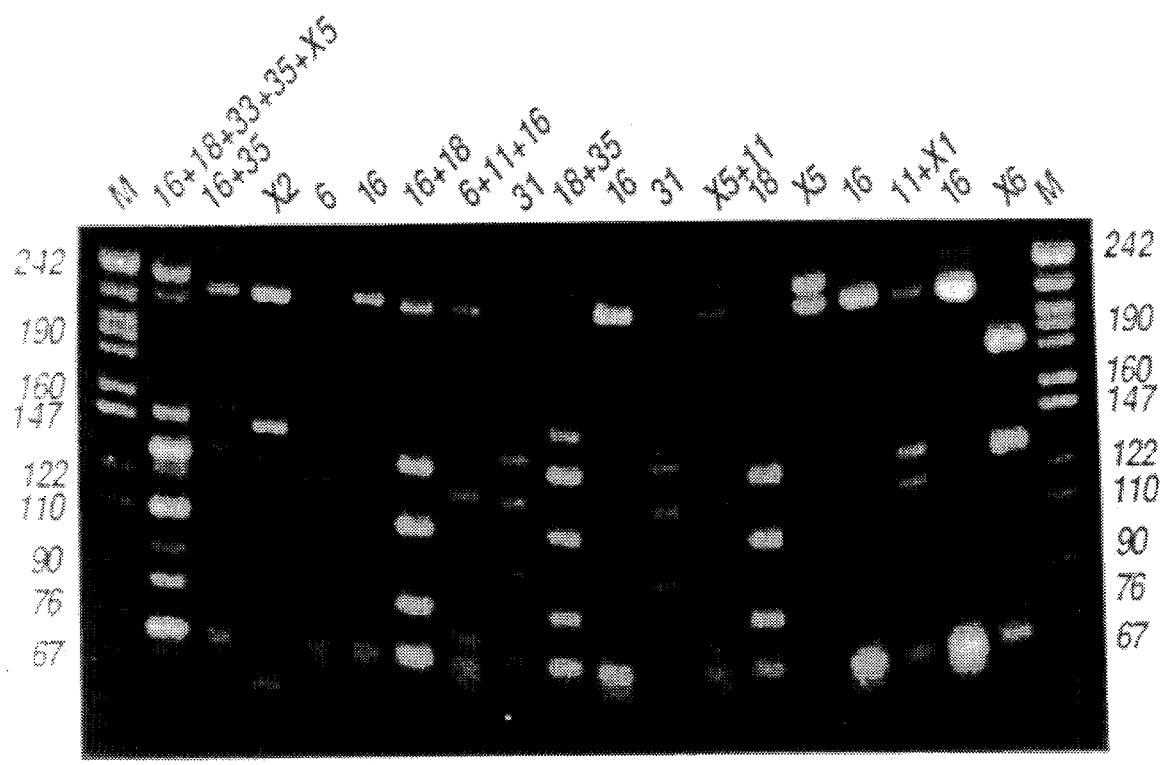

One of the major advantages of the RFLP analysis method of HPV typing is that it readily identifies cases with multiple types of HPV. A typical analytical gel is shown in FIG. 7. Although the lane marked X5 contains DNA from two viral types, the abundance of the second species is too low for accurate typing. Similarly, in the lane marked X5+11 there is a suggestion that HPV 6 DNA is present, although the abundance of this third species is too low for accurate assessment. In 22% of the cases of CIN 1, more than a single type of HPV was detected in an individual biopsy sample. Lesions containing multiple types of HPV were further classified as to which specific HPV types were detected (Table 4). Multiple types of HPV were detected much less frequently in CIN 2 or 3 lesions than in CIN 1 lesions. In only 7% of the cases of CIN 2 or 3 were multiple HPV types detected. Lesions containing multiple types of HPV were also further classified as to which specific HPV types were detected (Table 4).

Comment

The current results agree with the initial studies published from this and other laboratories that used Southern blot analysis to type the HPV associated with specific grades of CIN but disagree with more recent studies that have found a much higher degree of heterogeneity in HPV types associated with high-grade CIN [48, 25, 38, 56]. The reasons for the discrepancy between the current results and other recent studies are unclear, but may relate to a number of factors including the superiority of the PCR method for typing a particular HPV detected in a lesion and the fact that in this study all cervical biopsies were reviewed by a single pathologist. Because the cervical biopsies used for this study were obtained form a variety of sources, including a commercial laboratory that receives specimens from a broad geographic distribution, it is unlikely that the homogeneity of HPV types associated with CIN 2 and 3 lesions is secondary to geographic sampling.

These data support the hypothesis that the spectrum of cervical lesions referred to as CIN comprises two distinct and histologically separable entities [57]. One entity is "low-grade" CIN (CIN 1), which is associated with the high oncogenic risk HPV types 16, 18, or 33 in less than 30% of cases. The other entity is "high-grade" CIN (CIN 2 and CIN 3), which is associated with HPV types 16, 18, or 33 in almost 90% of cases. Because no differences were detected in the HPV types associated with lesions histologically classified as being CIN 2 or CIN 3, the commonly used histological distinctions between these two entities would appear to be meaningless. Combining CIN 2 and CIN 3 into a single clinicopathologic category called high-grade CIN that is distinct from low-grade CIN is not only consistent with the virologic data, but would also place histological terminology into conformity with the Bethesda System for classifying cervical cytology. The Bethesda System uses only two categories for cervical cancer precursors that have been termed "squamous intraepithelial lesions." [58].

The finding that either biopsy samples or cervicovaginal lavages from patients with low-grade CIN contain multiple types of HPV in many cases was unexpected as was the marked difference in the prevalence of multiple HPV types in low-grade as opposed to high-grade CIN lesions. In early studies that used either Southern blot hybridization or modified dot blot hybridization (Viratype, Digene Diagnostics Inc, Silver Spring, Md.) as a detection system, multiple types of HPV were found in a much smaller percentage of cases. For example, Lorincz et al. [49], who have combined clinical and virologic data from eight published studies, report that multiple HPV types occur in only 6.2% of HPV DNA-positive samples using Southern blot hybridization to assay for virus types. In contrast, investigators who used PCR have reported multiple HPV types in a much higher percentage of patients. Using PCR and type-specific primers for only HPV types 6, 11, 16, and 18, Burmer et al. [59] found multiple types in 9% of CIN 1 lesions and 15% of CIN 2 and 3 lesions. Gravitt et al. [60], who used L1 consensus sequence primers, but only a limited number of type-specific probes, detected multiple types in 14% of their HPV DNA-positive cases, and Bauer et al. [32], who also used L1 consensus sequence primers but a large number of type-specific probes, detected multiple types in 13% of HPV DNA-positive cases. Our study and the previous PCR reports differ in that in the other PCR studies, the material being amplified was derived from either a cervical swab or a cervicovaginal lavage, whereas in the current study, the starting material in most cases (89%) was derived from a small biopsy from an individual CIN lesion. We do not feel that differences in type of sample account for differences in the heterogeneity of HPV types in low- and high- grade lesions. Analysis of only biopsy samples detected 14% multiple types in low-grade lesions versus 6% multiple types in high-grade lesions. Therefore, the ratio of multiple types between low- and high-grade lesions is 1:2.3 in biopsy samples, which is very similar to the ratio of 1:2.75 for the study as a whole.

The finding of multiple HPV types in a significant percentage of biopsy specimens of individual lesions suggests that some of our current concepts about the pathogenesis of HPV-associated lesions of the anogenital tract need to be reevaluated. For example, in the currently widely quoted model of how an HPV-infected cell progresses to neoplasia, integration of the HPV genome into the host's DNA is considered to be a key event in most cases because it can disrupt the E2 open reading frame and lead to unregulated production of the E6 and E7 open reading frames [30, 47]. The continued expression or overexpression of E6 and E7 is thought to result in unregulated cell growth. If, however, multiple HPV types are present in an individual cell, and if an E2 repressing protein from one virus is able to control the transcription of both its own E6 and E7 open reading frames as well as those of other types of HPV present in the cell, then both E2 regions would have to be altered before neoplastic progression could occur. Such an interaction could explain the difference in frequency of single versus mixed HPV infections in low-grade lesions and high-grade lesions. Single E2 inactivation would be required for infections with one HPV type to progress, but multiple E2 inactivation events would be required in lesions containing mixed HPV infections. In order to understand the biologic implications of finding multiple HPV types in individual lesions, a high-resolution characterization of the location and state of individual HPV types in the cells from lesions with mixed infections will be required.

This study also suggests that the identification of HPV type may be used as a significant determinant of how patients with low-grade CIN are managed. In natural history studies of low-grade CIN, it has been reported that the biologic behavior of this lesion is heterogeneous. Although approximately two thirds of low-grade CIN lesions regress in the absence of treatment, in up to 20% of women, low-grade lesions will progress [61, 62]. Histological or cytological markers that allow discrimination between the low-grade lesions that will progress and those that will regress have not been identified. Based on the initial published associations between low-grade CIN and low oncogenic risk HPV types and high-grade CIN and high oncogenic risk HPV types, some investigators have suggested that HPV type might predict the behavior of low-grade CIN. In support of this hypothesis, two prospective follow-up studies have reported that low-grade CINs associated with HPV 16 or 18 are more likely to progress than lesions associated with HPV 6 or 11 [63, 64]. Unfortunately, the evidence relating HPV type to natural history is ambiguous since in most studies, only small numbers of patients were followed and methods were used that do not accurately type the HPV that is present.

In the current study we have used a highly accurate method for typing HPV and have investigated a relatively large number of cases of CIN. It is clear that high-grade CIN is homogeneous with respect to associated HPV types and that the vast majority (88%) of high-grade CINs contain either HPV 16, 18, or 33. In contrast, less than 30% of low-grade CIN lesions contain these HPV types. This would suggest that the likelihood of a low-grade CIN that lacks HPV 16, 18, or 33 progressing to a high-grade CIN is quite small, albeit measurable. These data might be interpreted as suggesting that it is unnecessary to treat low-grade lesions that lack HPV 16, 18, or 33, since such lesions should have a very low risk of progression. However, it is important to point out that there are not sufficient follow-up data to predict clinical outcome in low- or high-grade lesions associated with different HPV types. Until this information is available, a recommendation with regard to using HPV type to determine therapy cannot be made. Moreover, there are other important considerations that also need to be accounted for when deciding whether or not to treat a low-grade CIN. These must include the facts that the patient has a sexually transmitted disease, that many patients would prefer to be treated rather than undergo prolonged clinical follow-up, and that it may be more cost-effective to treat the patient than to follow her prospectively. Whatever final management algorithms are agreed on when data from follow-up studies become available, the implementation of protocols based on HPV type would be dependent on the availability of sensitive and highly accurate methods for detecting and typing HPV in clinical samples on a commercial basis.

These studies were supported by grant CA23767 from the National Institutes of Health, Bethesda, Md., and a grant from the American Cancer Society (Dr. Silverstein), grant 001368-10R6 from the American Foundation for AIDS Research, Los Angeles, Calif., and grant CCU206822 from the Centers for Disease Control, Atlanta, Ga. (Dr. Wright).

TABLE 3

Associations Of Histologic Findings With The Presence Of One Or More Specific Types of Human Papillomavirus (HPV)*

|  | CIN 1 | CIN 2 | CIN 3 |
| --- | --- | --- | --- |
| Individual HPV Types |  |  |  |
| 6 | 8 | — | — |
| 11 | 7 | 1 | — |
| 16 | 16 | 48 | 79 |
| 18 | 3 | 4 | 2 |
| 31 | 16 | 3 | 3 |
| 33 | — | 7 | 6 |
| 35 | 2 | — | 1 |
| 44 | 1 | — | — |
| 51 | 2 | 1 | 1 |
| 57 | 4 | — | — |
| N | 19 | 3 | 4 |
| Multiple | 22 | 7 | 6 |
| HPV Types |  |  |  |
| Total | 100 | 74 | 102 |

In Table 3, *CIN indicates cervical intraepithelial neoplasia, and N, novel HPV types whose restriction endonuclease patterns do not match any of the known types we have amplified or determined from the published sequence including HPVs 1, 2, 3, 6, 8, 10a, 11, 12, 14, 15, 16, 17, 18, 19, 20, 21, 22, 24a, 31, 33, 34, 35, 39, 41, 42, 43, 44, 45, 47, 51, 55a, and 57.

TABLE 4

Distribution Of Specific Types Of Human Papillomavirus (HPV) In Cervical Lesions With Mixed HPV Infections

| HPV TYPES | CIN 1 | CIN 2 | CIN 3 |
|---|---|---|---|
| L + M | 3 | — | — |
| L + H | 1 | — | 1 |
| M + M | 3 | 2 | — |
| M + H | 6 | 3 | 2 |
| H + H | 3 | 1 | 1 |
| M + N | 1 | — | — |
| H + N | — | — | — |
| N + N | — | 1 | — |
| MUT | 5 | — | 2 |

In Table 4, *L indicates low oncogenic risk virus (HPVs 6 and 11); M, medium oncogenic risk virus (HPVs other than 6, 11, 16, 18, and 33); H, high oncogenic risk virus (HPVs 16, 18, and 33); N, a new type of HPV as described in the legend for Table 3; MUT, infections with multiple types of HPV that could not be typed; and CIN, cervical intraepithelial neoplasia.

EXAMPLE IV

DETECTION AND SPECIES IDENTIFICATION OF MYCOBACTERIA BY PCR-RFLp ANALYSIS

Introduction

Isolation and identification of mycobacteria species takes several weeks when culturing is required. An alternative method that requires less than 24 hours for identification is enzymatic amplification (PCR) [33] of mycobacterial DNA. However, speciation requires further analysis employing molecular hybridization with "species-specific" probes, analysis that tends to be cumbersome and time consuming. We have devised a rapid and easy method for determining the species of mycobacterium from amplified mycobacterial DNA. The method is based on restriction fragment length polymorphism (RFLP) analysis of the material amplified using primers complementary to the highly conserved mycobacterial genes [42, 43] encoding a 65 kDa protein, the chaperonin groEL.

Materials And Methods

Samples

DNAs prepared from 15 reference and 83 clinical samples were used. These clinical samples were sputum samples.

DNA Preparation

DNA was prepared as previously described [44]. One hundred thousand cultured Mycobacteria bacilli were resuspended in 50 µl of TE-Triton (10 mM Tris-HCl pH 8, 1 mM EDTA, 1% Triton X-100) and boiled for 30 minutes. The samples were than centrifuged for 1 minute and 10 µl of crude lysate was used in the PCR reaction.

DNA Amplification

DNA was amplified in an automated thermocycler (Perkin-Elmer Cetus Corp) in a 50 µl reaction mixture containing 10 mM Tris-HCl pH 8.3, 50 mM KCl, 1.5 mM MgCl$_2$, 0.001% Gelatin, 200 µM of each dNTP, 0.5 µM of each primer and 2.5 U Taq DNA polymerase (Promega) for 40 cycles of denaturing for 1 minutes at 94° C. and of annealing/extension for 2 minutes at 60° C. A predenaturing step of 3 minutes at 94° C. and a final extension step of 10 minutes at 60° C. were included.

RFLP Analysis

Twenty U of Hae III or Bam HI restriction endonucleases (New England Biolabs) were added directly to the amplification reaction and the mixture was incubated at 37° C. in the thermocycler for 2 hours. Twenty-five µl of the restriction endonuclease reaction was then analyzed by electrophoresis at 100 V in a 3% 5/1 Nu Sieve/Sea Plaque GTG agarose gel containing 0.2 µg/ml of ethidium bromide prepared in Tris-Borate (89 mM Tris, 89 mM Boric Acid and 1 mM Na$_2$EDTA).

Selection Of Primers And Restriction Endonucleases

The amplification primers (Table 5) were designed using the published sequences of the groEl gene [42, 43] coding for the 65 kDa antigen of *Mycobacterium tuberculosis* and *Mycobacterium leprae*. The nucleotide sequences of the two genes were aligned for comparison and consensus sequences that would amplify both of these genes were selected. The restriction endonucleases were empirically selected. Cleavage analysis of DNA amplified from several different species of Mycobacteria showed that digestion with Hae III and Bam HI could differentiate between almost all species of Mycobacteriacae examined in this study.

Results And Discussion

Figure 8A:
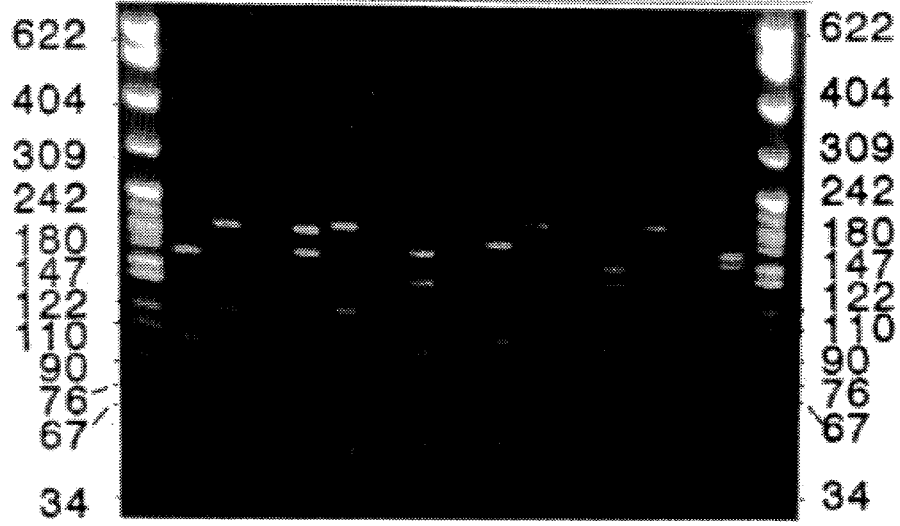
Figure 8B:
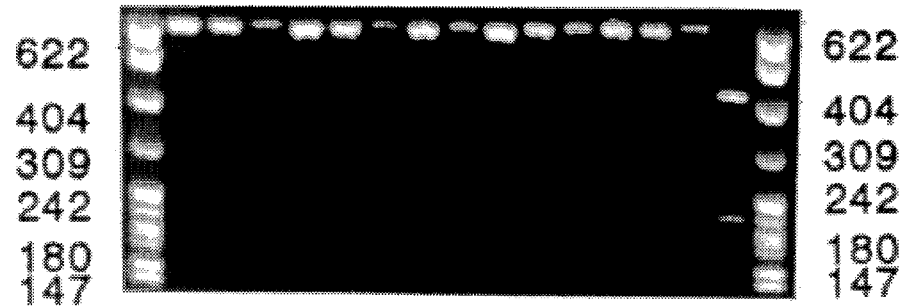

The primers used in this study amplify DNA from all samples examined and RFLP analysis identified the species in all clinical samples and discriminated between almost all reference samples. The material amplified from three of the clinical samples (one MTB and two Mycobacterium aviumintracellularae) was insufficient for RFLP analysis. In summary PCR/RFLP analysis offers a rapid and sensitive test for the detection and speciation of Mycobacteria in clinical samples. See FIG. 8 and FIG. 9.

TABLE 5

Nucleotide Sequences And Positions Of The Amplification Primers

| | |
|---|---|
| SEQ ID NO:14: | 20 |
| GAGGAATCAC TTCGCAATGG | |
| Primer: MB-5' | |
| Position: 236 - 255 | |
| SEQ ID NO:15: | 20 |
| ATGTAGCCCT TGTCGAACCG | |
| Primer: MB-3' | |
| Position: 844 - 825 | |

In Table 5, the sequences and positions were determined using the data from Shinnick, T. M., The 65-Kilodalton antigen of Mycobacterium tuberculosis, *Journal of Bacteriology*, 1987; vol. 169, pages 1080–1088, (Reference 42). In Table 5, the 5' primer is sense while 3' primer is antisense.

LIST OF REFERENCES

1. Migeon, C. J. Editorial: Comments about the need for prenatal treatment of congenital adrenal hyperplasia due to 21-hydroxylase deficiency, *Journal of Clinical Endocrinology and Metabolism*, 1990; vol. 70, no. 4, pages 836–837.
2. Carroll, M. C., Campbell, R. D., and Porter, R. R., Mapping of steroid 21-hydroxylase genes adjacent to complement component C4 genes in HLA, the major histocompatibility complex in man, *Proceedings of the National Academy of Science, USA*, 1985; vol. 82, no. 2, pages 521–525.

3. White, P. C., Grossberger, D., Onufer, B. J., Chaplin, D. C., New, M. I., Dupont, B., and Strominger, J. L., Two genes encoding steroid 21-hydroxylase are located near the genes encoding the forth component of complement in man, *Proceedings of the National Academy of Science, USA,* 1985; vol. 82, no. 4, pages 1089–1093.

4. Higashi, Y., Yoshioka, H., Yamane, M., Gotoh, O., and Fujii-Kurijama, Y., Complete nucleotide sequence of two steroid 21-hydroxylase genes tandemely arranged in human chromosome 6: a pseudogene and a genuine gene, *Proceedings of the National Academy of Science, USA,* 1986; vol. 83, no. 9, pages 2841–2845.

5. White, P. C., New, M. I., and Dupont, B., Structure of human steroid 21-hydroxylase genes, *Proceedings of the National Academy of Science, USA,* 1986; vol. 83, no. 14, pages 5111–5115.

6. Tusie-Luna, M. T., Speiser, P. W., Dumic, M., New, M. I., and White, P. C., A Mutation (Pro-30 to Leu) in CYP21 Represents a Potential Nonclassic Steroid 21-Hydroxylase Deficiency Allele, *Molecular Endocrinology,* 1991; vol. 5, no. 5, pages 685–692.

7. Donohoue, P. A., Van Dop, C., McLean, R. H., White, P. C., Jospe, N., and Migeon, C. J., Gene conversion in salt-losing congenital adrenal hyperplasia with absent complement C4B protein, *Journal of Clinical Endocrinology and Metabolism,* 1986; vol. 62, no. 5, pages 995–1002.

8. Rumsby, G., Carroll, M. C., Porter, R. R., Grant, D. B., and Hjelm, M., Deletion of steroid 21-hydroxylase and Complement C4 genes in Congenital Adrenal Hyperplasia, *Journal of Medical Genetics,* 1986; vol. 23, pages 204–209.

9. Mornet, E., Boue, J., Raux-Demay, M., Couillin, P., Oury, J. F., Dumez, Y., Dausset, J., Cohen, D., and Boue, A., First trimester prenatal diagnosis of 21-hydroxylase deficiency by linkage analysis to HLA-DNA probes and by 17-hydroxyprogesterone determination, *Human Genetics,* 1986; vol. 73, no. 1, pages 358–364.

10. Donohoue, P. A., Jospe, N., Migeon, C. J., McLean, R. H., Bias, W. B., White, P. C., and Van Dop, C., Restriction maps and restriction fragment length polymorphisms of the human 21-hydroxylase genes, *Biochemical And Biophysical Research Communications,* 1986; vol. 136, no. 2, pages 722–729.

11. Werkmeister, J. W., New, M. I., Dupont, B., and White, P. C., Frequent deletion and duplication of the steroid 21-hydroxylase genes, *Am. J. Hum. Genet.,* 1986; vol. 39, pages 461–469.

12. Boehm, B. O., Rosak, C., Boehm, T. L. J., Kuehnl, P., White, P. C., Schoffling, K., Classical and late-onset forms of congenital adrenal hyperplasia caused by 21-OH deficiency reveal different alterations in the C4/21-OH gene region, *Molecular Biology & Medicine,* 1986; vol. 3, pages 437–448.

13. Jospe, N., Donohoue, P. A., Van Dop, C., McLean, R. H., Bias, W. B., and Migeon, C. J., prevalence of polymorphic 21-hydroxylase gene (CA21HB) mutations in salt-losing congenital adrenal hyperplasia, *Biochemical And Biophysical Research Communications,* 1987; vol. 142, no. 3, pages 798–804.

14. Matteson, K. J., Phillips, III, J. A., Miller, W. L., Chung, B. C., Orlando, P. J., Frisch, H., Ferrandez, A., and Burr, I. M., p45OXXI (steroid 21-hydroxylase) gene deletions are not found in family studies of congenital adrenal hyperplasia, *Proceedings of the National Academy of Science, USA,* 1987; vol. 84, pages 5858–5862.

15. Amor, M., parker, K. L., Globerman, H., New, M. I., and White, P. C., Mutation in the CYP21B gene (Ile-172Asn) cause steroid 21-hydroxylase deficiency, *Proceedings of the National Academy of Science USA,* 1988; vol. 85, pages 1600–1604.

16. White, P. C., Vitek, A., Dupont, B., and New, M. I., Characterization of frequent deletions causing steroid 21-hydroxylase deficiency, *Proceedings of the National Academy of Science USA,* 1988; vol. 85, pages 4436–4440.

17. Speiser, P. W., New, M. I., and White, P. C., Molecular genetic analysis of nonclassic steroid 21-hydroxylase deficiency associated with HLA-B14,DR1, *New England Journal of Medicine,* 1988; vol. 319, no. 1, pages 19–23.

18. Higashi, Y., Tanae, A., Inoue, H., and Fujii-Kuriyama, Y., Evidence for frequent gene conversion in the steroid 21-hydroxylase p-450(C21) gene: implications for steroid 21-hydroxylase deficiency, *American Journal of Human Genetics,* 1988; vol. 42, no. 1, pages 17–25.

19. Higashi, Y., Inoue, A., Hiromasa, T., and Fujii-Kurijama, Y., Aberrant splicing and missense mutation causing steroid 21-hydroxylase-(P-450c21) deficiency in humans: possible gene conversion products, *Proceedings of the National Academy of Science, USA,* 1988; vol. 85, pages 7486–7490.

20. Owerbach, D., Crawford, Y. M., and Draznin, M. B., Direct analysis of CYP21B genes in 21-hydroxylase deficiency using polymerase chain reaction amplification, *Molecular Endocrinology,* 1990; vol. 4, no. 1, pages 125–131.

21. Speiser, P. W., Laforgia, N., Kato, K., Pareira, J., Khan, R., Yang, S. Y., Whorwood, C., White, P. C., Elias, S., Schriock, E., Schriock, E., Simpson, J. L., Taslimi, M., Najjar, J., May, S., Mills, G., Crawford, C., and New, M. I., First trimester prenatal treatment and molecular genetic diagnosis of congenital adrenal hyperplasia (21-hydroxylase deficiency), *Journal of Clinical Endocrinology and Metabolism,* 1990; vol. 70, no. 4, pages 838–848.

22. Mornet, E., Crete, P., Kuttenn, F., Raux-Demay, M. C., Boue, J., White, P. C., and Boue, A., Distribution of deletions and seven point mutations on CYP21B genes in three clinical forms of steroid 21-hydroxylase deficiency, *American Journal of Human Genetics,* 1991; vol. 48, no. 1, pages 79–88.

23. Boshart, M., Gissmann, L., Ikenberg, H., Kleinheinz, A., Scheurlen, W., and zur Hausen, H., A new type of papillomavirus DNA, its presence in genital cancer biopsies and in cell lines derived from cervical cancer, *EMBO Journal,* 1984; vol. 3, no. 5, pages 1151–1157.

24. Gissman, L. and Schneider, A., Human papillomavirus DNA in preneoplastic and neoplastic genital lesions, in Peto, R., and zur Hausen, H. (editors), *Viral Etiology of Cancer,* Cold Spring Harbor Laboratory, Cold Spring Harbor, N.Y., 1986; pages 217–224.

25. Reid, R., Greenberg, M., Jenson, A. B., Husain, M., Willett, J., Daoud, Y., Temple, G., Stanhope, C. R., Sherman, A. I., Phibbs, G. D., and Lorincz, A. T., Sexually transmitted papillomaviral infections I. The anatomic distribution and pathologic grade of neoplastic lesions associated with different viral types, *American Journal of Obstetrics and Gynecology,* 1987; vol. 156, pages 212–222.

26. Gissman, L. and zur Hausen, H., Partial characterization of viral DNA from genital warts (condyloma acuminatum), *International Journal of Cancer,* 1980; vol. 25, pages 605–609.

27. DeVilliers, E. M., Gissman, L., and zur Hausen, H., Molecular cloning of viral DNA from human genital warts, *Journal of Virology,* 1981; vol. 40, pages 932–935.

28. Gissman, L., Wolnik, L., Ikenberg, H., Koldovsky, U., Schnurch, H. G., and zur Hausen, H., Human papillomavirus types 6 and 11 DNA sequences in genital and laryngeal papillomas and in some cervical cancers, *Proceedings of the National Academy of Science, USA*, 1983; vol. 72, pages 560–563.
29. Manos, M. M., Ting, Y., Wright, D. K., Lewis, A. J., Broker, T. R., and Wolinsky, S. M., Use of polymerase chain reaction amplification for the detection of genital human papillomaviruses, *Cancer Cells*, 1989; vol. 7, pages 209–214.
30. Koutsky, L. A., Galloway, D. A., and Holmes, K. K., Epidemiology of genital human papillomavirus infection, *Epidemiologic Reviews*, 1988; vol. 10, pages 123–163.
31. Reid, R. and Lorincz, A. T., Should physicians test for HPV, *Journal of Family Practice*, 1991; vol. 32, pages 183–191.
32. Bauer, H. M., Ting, Y., Greer, C. E., Chambers, J. C., Tashiro, C. J., Chimera, J., Reingold, A., and Manos, M. M., Genital human papillomavirus infection in female university students as determined by a PCR-based method, *Journal of the American Medical Association*, 1991; vol. 265, pages 472–477.
33. Saiki, R. K., Scharf, S., Paloona, F., Mullins, K. B., Horn, G. T., Erlich, H. A., and Arnheim, N., Enzymatic amplification of β-globin genomic sequences and restriction site analysis for diagnosis of sickle cell anemia, *Science*, 1985; vol. 230, pages 1350–1354.
34. Sambrook. J., Fritsch, E. F., and Maniatis, T., Analysis and cloning of eukaryotic genomic DNA, in *Molecular Cloning, A Laboratory Manual Volume II*, Cold Spring Harbor Laboratory Press, Cold Spring Harbor, N.Y., 1989; 9:14–9:22.
35. Haliassos, A., Chomel, J. C., Grandjouan, S., Kruh, J., Kaplan, J. C., and Kitzis, A., Detection of minority point mutations by modified PCR technique: a new approach for a sensitive diagnosis of tumor-progression markers, *Nucleic Acids Research*, 1989; vol. 17, no. 20, pages 8093–8099.
36. Lungu, O. and Silverstein, S., A PCR strategy that differentiates two alleles for a single base insertion within a T repeats, *Biotechniques*, 1992, accepted for publication.
37. Maniatis, T., Fritsch, E. F., and Sambrook, J., *Molecular Cloning, A Laboratory Manual*, Cold Spring Harbor Laboratory, Cold Spring Harbor, N.Y., 1982.
38. Crum, C. P., Mitao, M., Levine, R. U., and Silverstein, S., Cervical papillomaviruses segregate within morphologically distinct precancerous lesions, *Journal of Virology*, 1985; vol. 54, pages 675–681.
39. Ting, Y. and Manos, M. M., Detection and typing of genital human papillomaviruses, in Innis, M. A., Gelfand, M., Sninsky, J., and White, T., editors, *PCR Protocols: A Guide To Methods And Applications*, Academic Press Inc., San Diego, Calif., 1990; pages 356–367.
40. Jiang, W., Kahn, S., Guillem, J., Lu, S. H., and Weinstein, I. B., Rapid detection of ras oncogenes in human tumors: applications to colon, esophageal and gastric cancer, Oncogene, 1989; vol. 4, pages 923–928.
41. Lungu, O., Crum, C. P., and Silverstein, S., Biologic properties and nucleotide sequence analysis of human papillomavirus type-51, *Journal of Virology*, 1991; vol. 65, pages 4216–4225.
42. Shinnick, T. M., The 65-Kilodalton antigen of Mycobacterium tuberculosis, *Journal of Bacteriology*, 1987; vol. 169, pages 1080–1088.
43. Mehra, V., Sweeter, D., and Young, R. A., Efficient mapping of protein antigenic determinants, *Proceedings of the National Academy of Science, USA*, 1986; vol. 83, pages 7013–7017.
44. Sritharan, V. and Barker, Jr., R. H., A simple method for diagnosing M. tuberculosis infection in clinical samples using PCR, *Molecular and cellular Probes*, 1991; vol. 5, pages 385–395.
45. Lungu, O., Wright, Jr., T. C., and Silverstein, S., Typing Of Human Papillomaviruses By Polymerase Chain Reaction Amplification With L1 Consensus Primers And RFLP Analysis, *Molecular And Cellular Probes*, 1992; vol. 6, pages 145–152.
46. Lungu, O., Sun, X. W., Felix, J., Rechart, R. M., Silverstein, S., Wright, Jr., T. C., Relationship Of Human Papillomavirus Type To Grade Of Cervical Intraepithelial Neoplasia, *Journal of the American Medical Association*, 1992; vol. 267, pages 2493–2496.
47. Wright, T. C., Richart, R. M., Role of human papillomavirus in the pathogenesis of genital tract warts and cancer, Gynecologic Oncology, 1990; vol. 37, pages 151–164.
48. Lorincz A. T., Temple, G. F., Kurman, R. J., Jenson, A. B., Lancaster, W. D., Oncogenic association of specific human papillomavirus types with cervical neoplasia, *Journal of the National Cancer Institute*, 1987; vol. 79, pages 671–677.
49. Lorincz, A. T., Reid, R., Jenson, A. B., Greenberg, M. D., Lancaster, W., Kurman, R. J., Human papillomavirus infection of the cervix: relative risk associations of 15 common anogenital types, *Obstetrics & Gynecology*, 1992; vol. 79, no. 3, pages 328–337.
50. Roman A., Fife, K. H., Human papillomaviruses: are we ready to type, *Clinical Microbiology Reviews*, 1989; vol. 2, no. 2, pages 166–190.
51. Singer, A., Jenkins, D., Viruses and cervical cancer, *British Medical Journal*, 1991; vol. 302, no. 770, pages 251–252.
52. Ferenczy, A., Winkler, B., Cervical intraepithelial neoplasia and condyloma, in Kurman R., editor, *Blaustein's Pathology of the Female Genital Tract*, New York, N.Y., Springer Verlag; 1987:191.
53. Franquemont, D. W., Ward, B. E., Andersen, W. A., Crum, C. P., Prediction of 'high risk' cervical papillomavirus infection by biopsy morphology, *American Journal of Clinical Pathology*, 1989; vol. 92, no. 5, pages 577–582.
54. Richart, R. M., Nuovo, G. J., Human Papillomavirus DNA in situ hybridization may be used for the quality control of genital tract biopsies, *Obstetrics & Gynecology*, 1989; vol. 75, no. 2, pages 223–226.
55. Willett, G. D., Kurman, R. J., Reid, R., Greenberg, M., Jenson, A. B., and Lorincz, A. T., Correlation of the histologic appearance of intraepithelial neoplasia of the cervix with human papillomavirus types, *International Journal of Gynecological Pathology*, 1989; vol. 8, no. 1, pages 18–25.
56. Nuovo, G. J., Friedman, D., Richart, R. M., In situ hybridization analysis of human papillomavirus DNA segregation patterns in lesions of the female genital tract, *Gynecologic Oncology*, 1990; vol. 36, no. 2, pages 256–262.
57. Richart, R. M., Clinical commentary: a modified terminology for cervical intraepithelial neoplasia, *Obstetrics & Gynecology*, 1990; vol. 75, pages 131–133.
58. NCI Workshop, The Bethesda System for reporting cervical/vaginal cytologic diagnoses, *Journal of the American Medical Association*, 1989; vol. 262, pages 931–934.
59. Burmer, G. C., Parker, J. D., Bates, J., East, K., Kulander, B. G., Comparative analysis of human papillomavirus detection by polymerase chain reaction and Virapap/Viratype kits, *American Journal of Clinical Pathology*, 1990; vol. 94, no. 5, pages 554–560.

60. Gravitt, P., Hakenewerth, A., Stoerker, J., A direct comparison of methods proposed for use in widespread screening of human papillomavirus infections, *Molecular And Cellular Probes,* 1991; vol. 5, pages 65–72.
61. Nasiell, K., Behavior of mild cervical dysplasia during long-term follow-up, *Obstetrics & Gynecology,* 1986; vol. 67, pages 665–669.
62. Barron, B. A., Richart, R. M., A statistical model of the natural history of cervical carcinoma based on a prospective study of 557 cases, Journal of the National Cancer Institute, 1968; vol. 41, pages 1343–1353.
63. Campion, M. J., Cuzick, J., McCance, D. J., Singer, A., Progressive potential of mild cervical atypia: prospective, cytological, colposcopic, and virologic study, *The Lancet,* 1986; vol. 2, no. 8501, pages 237–240.
64. Syrjanen, K. J., Natural history of genital human papillomavirus infections, Papillomavirus Rep., 1991; vol. 1, pages 1–4.

What is claimed is:

1. A method for detecting the presence of mycobacteria in a clinical sample which comprises:
   (a) obtaining a clinical sample containing nucleic acid molecules;
   (b) amplifying the nucleic acid molecules in the sample by Polymerase Chain Reaction (PCR) with an amplification primers GAGGAATCACTTCGCAATGG (SEQ ID NO: 14) and ATGTAGCCCTTGTCGAACCG (SEQ ID NO:15);
   (c) treating the resulting amplified nucleic acid molecules with a restriction endonuclease selected from the group consisting of Hae III and BamHI to produce nucleic acid restriction fragments; and
   (d) analyzing the nucleic acid restriction fragments so produced using Restriction Fragment Length Polymorphism (RFLP) analysis so as to detect the presence of mycobacterium in the clinical sample.

2. The method of claim 1, wherein the nucleic acid is selected from the group consisting of DNA and mRNA.

3. The method of claim 1, wherein the clinical sample is a sputum sample.

4. A method for determining the type of mycobacteria present in a clinical sample containing mycobacteria which comprises:

(a) obtaining a clinical sample containing mycobacteria;
   (b) obtaining from the clinical sample a nucleic acid molecule-containing sample,
   (c) amplifying the nucleic acid molecules in the resulting sample by Polymerase Chain Reaction (PCR) using amplification primers GAGGAATCACTTCGCAATGG (SEQ ID NO: 14) and ATGTAGCCCTTGTCGAACCG (SEQ ID NO:15);
   (d) treating the resulting amplified nucleic acid molecules with a restriction endonuclease selected from the group consisting of Hae III and Bam HI to produce nucleic acid restriction fragments; and
   (e) analyzing the nucleic acid restriction fragments so produced using Restriction Fragment Length Polymorphism (RFLP) analysis so as to determine the type of mycobacteria present in the clinical sample.

5. The method of claim 4, wherein the nucleic acid is selected from the group consisting of DNA and mRNA.

6. The method of claim 4, wherein the clinical sample is a sputum sample.

* * * * *